United States Patent
Xue et al.

(10) Patent No.: US 11,958,831 B2
(45) Date of Patent: Apr. 16, 2024

(54) PYRAZOLE COMPOUNDS, PHARMACEUTICAL COMPOSITIONS THEREOF AND USE THEREOF

(71) Applicant: ARTIVILA (SHENZHEN) INNOVATION CENTER, LTD., Guangdong (CN)

(72) Inventors: Chubiao Xue, Guangdong (CN); Liye Huang, Guangdong (CN); Hua Li, Guangdong (CN); Tao Li, Guangdong (CN); Huabin Liu, Guangdong (CN)

(73) Assignee: ARTIVILA (SHENZHEN) INNOVATION CENTER, LTD., Shenzhen (CN)

( * ) Notice: Subject to any disclaimer, the term of this patent is extended or adjusted under 35 U.S.C. 154(b) by 566 days.

(21) Appl. No.: 17/271,397

(22) PCT Filed: Aug. 22, 2019

(86) PCT No.: PCT/CN2019/102067
§ 371 (c)(1),
(2) Date: Feb. 25, 2021

(87) PCT Pub. No.: WO2020/043008
PCT Pub. Date: Mar. 5, 2020

(65) Prior Publication Data
US 2021/0340124 A1 Nov. 4, 2021

(30) Foreign Application Priority Data
Aug. 27, 2018 (CN) .......................... 201810992017.8

(51) Int. Cl.
*C07D 401/14* (2006.01)
*A61K 45/06* (2006.01)

(52) U.S. Cl.
CPC ............ *C07D 401/14* (2013.01); *A61K 45/06* (2013.01)

(58) Field of Classification Search
CPC .................................................. C07D 401/14
See application file for complete search history.

(56) References Cited

FOREIGN PATENT DOCUMENTS

| CN | 107438603 A | 12/2017 |
|---|---|---|
| RU | 2604062 C2 | 12/2016 |
| WO | 2016172560 A1 | 10/2016 |
| WO | 2016/210036 A1 | 12/2016 |
| WO | 2018/081294 A1 | 5/2018 |
| WO | 2018/089199 A1 | 5/2018 |

OTHER PUBLICATIONS

Interleukin-1 receptor associated kinase [online] retrieved from the internet on Sep. 27, 2023; URL: https://en.wikipedia.org/wiki/Interleukin-1_receptor_associated_kinase.*
International Search Report issued in PCT/CN2019/102067 dated Nov. 27, 2019.
Adams, et al.: "IRAK1 is a novel DEK transcriptional target and is essential for head and neck cancer cell survival", Oncotarget 6(41), (2015), pp. 43395-43407.
Beverly and Starczynowski: "IRAK1: oncotarget in MDS and AML", Oncotarget 5(7), (2014), pp. 1699-1700.
Cameron, et al.: "Loss of Interleukin Receptor-Associated Kinase 4 Signaling Suppresses Amyloid Pathology and Alters Microglial Phenotype in a Mouse Model of Alzheimer's Disease", J. of Neuroscience 32(43), (2012), pp. 15112-15123.
Cheng, et al.: "IRAK1 Augments Cancer Stemness and Drug Resistance via the AP-1/AKR1B10 Signaling Cascade in Hepatocellular Carcinoma", Cancer Res. 78(9), (2018), pp. 2332-2342.
Dissiau, et al.: "Targeting IRAK1 in T-Cell acute lymphoblastic leukemia", Oncotarget 6(22), (2015), pp. 18956-18965.
Dudhgaonkar, et al.: "Selective IRAK4 Inhibition Attenuates Disease in Murine Lupus Models and Demonstrates Steroid Sparing Activity", J. Immunol. 198 (2017), pp. 1308-1319.
Jimenez, et al.: "MYD88 L265P is a marker highly characteristic of, but not restricted to, Waldenstroem's macroglobulinemia", Leukemia 27, (2013), pp. 1722-1728.
Kelly, et al.: "Selective interleukin-1receptor-associated kinase 4 inhibitors for the treatment of autoimmune disorders and lymphoid malignancy", JEM: J. Exp. Med. 212(13), (2015), pp. 2189-2201.
Kim, et al.: "A critical role for IRAK4 kinase activity in Toll-like receptor-mediated innate immunity", JEM 204(5), (2007), pp. 1025-1036.
Koziczak-Holbro, et al.: "The Critical Role of Kinase Activity of Interleukin-1 Receptor-Associated Kinase 4 in Animal Models of Joint Inflammation", Arthritis & Rheumatism, 60(6), (2009), pp. 1661-1671.

(Continued)

*Primary Examiner* — Shawquia Jackson
(74) *Attorney, Agent, or Firm* — Norton Rose Fulbright US LLP; James R. Crawford

(57) ABSTRACT

Disclosed are pyrazole compounds represented by formula (I), pharmaceutical compositions containing such compounds, a method for preparing such compounds, and use of the pyrazole compounds and the pharmaceutical compositions. Such compounds are useful for inhibiting IRAK family kinases, and also useful for treating diseases caused by IRAK family kinases, such as autoimmune diseases, inflammatory diseases and cancers.

(I)

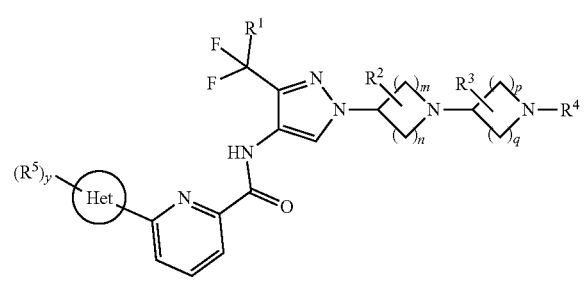

18 Claims, No Drawings

(56) References Cited

OTHER PUBLICATIONS

Li, et al.: "Inhibition of IRAK1/4 sensitizes T cell acute lymphoblastic leukemia to chemotherapies", J. Clin. Invest. 125 (3), (2015), pp. 1081-1097.

Liang, et al.: "Therapeutic Targeting of MLL Degradation Pathways in MLL-Rearranged Leukemia", Cell 168 (2017), pp. 59-72, e1-e6.

Ngo, et al.: "Oncogenically active MYD88 mutations in human lymphoma", Research Letter, Nature 470 (2011), pp. 115-121.

Rekhter, et al.: "Genetic ablation of IRAK4 kinase activity inhibits vascular lesion formation", Biochem. & Biophys. Res. Communications 367 (2008), pp. 642-648.

Rhyasen, et al.: "Targeting IRAK1 as a Therapeutic Approach for Myelodysplastic Syndrome", Cancer Cell 24 (2013), pp. 90-104.

Staschke, et al.: "IRAK4 Kinase Activity Is Required for Th17 Differentiation and Th17-Mediated Disease", J. Immunol. 183 (2009), pp. 568-577.

Tumey, et al.: "Identification and optimization of indolo[2,3-c]quinoline inhibitors if IRAK4", Bioorg. Med. Chem. Lett. 24 (2014), pp. 2066-2072.

Wee, et al.: "IRAK1 is a therapeutic target that drives breast cancer metastasis and resistance to paclitaxel", Nature Communications DOI: 10.1038/ncomms9746, (2015), pp. 1-15.

Yang, et al.: "A mutation in MYD88 (L265P) supports the survival of lymphoplasmacytic cells by activation of Bruton tyrosine kinase in Waldenstroem macroglobulinemia", Blood 12(7), (2013), pp. 1222-1232.

Yang, et al.: "Interleukin 1 receptor-associated kinase 1 (IRAK1) mutation is a common, essential driver for Kaposi sarcoma herpesvirus lymphoma", PNAS 112(18), (2015), pp. E4762-E4768.

Office Action dated Sep. 17, 2020 by the Russian Patent Office in the corresponding Patent Application No. 2021106215/04(013492), with English translation.

\* cited by examiner

PYRAZOLE COMPOUNDS, PHARMACEUTICAL COMPOSITIONS THEREOF AND USE THEREOF

This application is a national phase application under 35 U.S.C. § 371 of International Application No. PCT/CN2019/102067 filed Aug. 22, 2019, which claims priority under 35 U.S.C. 119 to Chinese Patent Application No. 201810992017.8 filed on Aug. 27, 2018. The entire contents of each of the above-referenced disclosures is specifically incorporated by reference herein without disclaimer.

TECHNICAL FIELD

The present application belongs to the field of chemical medicaments and relates to pyrazole compounds, pharmaceutically acceptable salts thereof, pharmaceutical compositions containing such compounds, and uses of such compounds or compositions for preparing medicaments.

BACKGROUND

The IRAK protein family consists of IRAK1, IRAK2, IRAK3, and IRAK4. IRAK1 and IRAK4 are active serine/threonine kinases and key signaling factors downstream of interleukin receptor-1 (IL-1R)/toll-like receptor (TLR) signaling pathway and play an important role in innate immunity. By contrast, IRAK2 and IRAK3 are pseudokinases. IRAK1 and IRAK4 are implicated in blood cancer. In some B-cell lymphomas, the activation of TLR/IRAK pathways generally occurs concurrently with gain-of-function mutation MYD88$^{L265P}$. This mechanism occurs in Waldenström's macroglobulinaemia (WM), diffuse large B-cell lymphoma (DLBCL), and primary effusion lymphoma (1-4). Some head and neck squamous cell carcinoma, liver cancer, and triple negative breast cancer also show increased IRAK1 concentration (5-7). In mouse models of liver cancer, the growth of HCC is suppressed by an IRAK1/4 inhibitor; and the tumor growth was synergistically suppressed when the IRAK1/4 inhibitor is administered in combination with sorafenib (7). MYD88/IRAK signaling plays an indispensable role in the survival of T-Cell Acute Lymphoblastic Leukemia (T-ALL) cells (8-9). The activation and overexpression of IRAK1 negatively affect prognosis in myelodysplastic syndrome (MDS) (8, 10). IRAK1 is overexpressed in acute myeloid leukemia (AML) (11). Studies prove that the inhibition of IRAK1/4 can reduce the growth of mixed-lineage leukemia-rearranged leukemic cells (12). These studies fully prove that IRAK1 and IRAK4 are targets for cancer treatment.

IRAK1 and IRAK4 are also targets for the treatment of autoimmune diseases. Genetically modified mice with IRAK4 deletion or expression of IRAK4 without kinase activity have an impaired immune response to TLR stimulation (such as the production of TNFα and IL-6 induced by LPS) (13). These mice are resistant to experimentally induced arthritis (14), atherosclerosis (15), and MOG-induced encephalomyelitis (16). Mice expressing IRAK4 without kinase activity are resistant to the development of Alzheimer's disease (17). An IRAK4 small molecule inhibitor exhibits an ability to inhibit TLR-induced inflammatory signaling in vivo and in vitro (18-19). The administration of an IRAK4 inhibitor can reduce gout-like inflammation in a model of peritonitis induced by uric acid (19) and can relieve diseases in a mouse model of lupus (20).

The present application provides an IRAK inhibitor with a new structure. Such inhibitors can inhibit IRAK4 kinase activity and be used for treating autoimmune diseases, inflammatory diseases, and cancer.

REFERENCES

1. Jimenez, C. et al., *Leukemia,* 2013, 27, 1722-1728.
2. Yang, G. et al., *Blood,* 2013, 122, 1222-1232.
3. Ngo, V. N. et al., *Nature,* 2011, 470, 115-119.
4. Yang, D. et al., *Proc. Natl. Acad. Sci. USA,* 2014, 111, E4762-4768.
5. Wee, Z. N. et al., *Nat. Commun.* 2015, 6, 8746.
6. Adams, A. K. et al., *Oncotarget,* 2015, 6, 43395-43407.
7. Cheng, B. Y. et al., *Cancer Res.* 2018, 78, 2332-2342.
8. Li, Z. et al., *J. Clin. Invest.* 2015, 125, 1081-1097.
9. Dussiau, C. et al., *Oncotarget,* 2015, 6, 18956-18965.
10. Rhyasen, G. W. et al., *Cancer Cell,* 2013, 24, 90-104.
11. Beverly, L. J. et al., *Oncotarget,* 2014, 5, 1699-1700.
12. Liang, K. et al., *Cell,* 2017, 168, 59-72 e13.
13. Kim, T. W. et al., *J. Exp. Med.* 2007, 204, 1025-1036.
14. Koziczak-Holbro, M. et al., *Arthritis Rheum.* 2009, 60, 1661-1671.
15. Rekhter, M. et al., *Biochem. Biophys. Res. Commun.* 2008, 367, 642-648.
16. Staschke, K. A. et al., *J. Immunol.* 2009, 183, 568-577.
17. Cameron, B. et al., *J. Neurosci.* 2012, 32, 15112-15123.
18. Tumey, L. N. et al., *Bioorg. Med. Chem. Lett.* 2014, 24, 2066-2072.
19. Kelly, P. N. et al., *J. Exp. Med.* 2015, 212, 2189-2201.
20. Dudhgaonkar, S. et al., *J. Immunol.* 2017, 198, 1308-1319.

SUMMARY

The present application provides a compound represented by Formula (I) or a pharmaceutically acceptable salt thereof, wherein the compound represented by Formula (I) has the following structure:

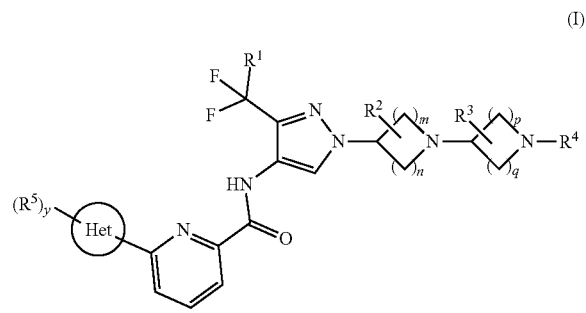

wherein
the Het ring is a five- or six-membered heteroaromatic ring;
$R^1$ is selected from H or D;
$R^2$ and $R^3$ are each selected from H, D, alkyl, halogen, or $OR^a$;
$R^4$ is selected from $COR^d$, $CONR^bR^c$, $CO_2R^d$, $SO_2R^d$, or $SO_2NR^bR^c$;
$R^5$ is selected from H, D, halogen, cyano, $OR^a$, $SR^a$, $NR^bR^c$, $COR^d$, $CONR^bR^c$, $CO_2R^d$, $SO_2R^d$, $SO_2NR^bR^c$, alkyl, alkenyl, alkynyl, cycloalkyl, or heterocycloalkyl; wherein the alkyl, alkenyl, alkynyl, cycloalkyl, or heterocycloalkyl is unsubstituted or substituted with 1 to 3 $R^{5a}$;

$R^{5a}$ is selected from H, D, halogen, cyano, alkyl, alkenyl, alkynyl, cycloalkyl, heterocycloalkyl, $OR^a$, $SR^a$, $NR^bR^c$, $COR^d$, $CONR^bR^c$, $CO_2R^d$, $SO_2R^d$, or $SO_2NR^bR^c$; wherein the alkyl, cycloalkyl, or heterocycloalkyl is unsubstituted or substituted with 1 to 3 $R^{5b}$;

$R^{5b}$ is selected from H, D, halogen, cyano, $OR^a$, $SR^a$, $NR^bR^c$, $COR^d$, $CONR^bR^c$, $CO_2R^d$, $SO_2R^d$, or $SO_2NR^bR^c$;

$R^a$, $R^b$, $R^c$, and $R^d$ are each selected from H, D, alkyl, alkenyl, alkynyl, cycloalkyl, heterocycloalkyl, aryl, or heteroaryl, wherein the alkyl, alkenyl, alkynyl, cycloalkyl, heterocycloalkyl, aryl, or heteroaryl is unsubstituted or substituted with 1 to 4 $R^6$;

$R^6$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl;

wherein $R^b$ and $R^c$ in a group containing both $R^b$ and $R^c$ are attached to a N atom in the group by a single bond or form a heterocycloalkyl together with the N atom to which they are attached, and the heterocycloalkyl is unsubstituted or substituted with 1 to 3 $R^7$;

$R^7$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl; and m, n, p, q, and y are each independently 1, 2, or 3.

Preferably, the compound provided by the present application has a structure represented by Formula (IA):

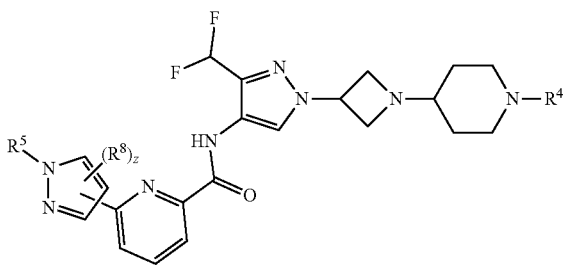

(IA)

wherein $R^4$ is selected from $COR^d$, $CONR^bR^c$, $CO_2R^d$, $SO_2R^d$, or $SO_2NR^bR^c$; $R^5$ is selected from H, D, halogen, cyano, $OR^a$, $SR^a$, $NR^bR^c$, $COR^d$, $CONR^bR^c$, $CO_2R^d$, $SO_2R^d$, $SO_2NR^bR^c$, alkyl, alkenyl, alkynyl, cycloalkyl, or heterocycloalkyl; wherein the alkyl, alkenyl, alkynyl, cycloalkyl, or heterocycloalkyl is unsubstituted or substituted with 1 to 3 $R^{5a}$;

$R^{5a}$ is selected from H, D, halogen, cyano, alkyl, alkenyl, alkynyl, cycloalkyl, heterocycloalkyl, ORE, $SR^a$, $NR^bR^c$, $COR^d$, $CONR^bR^c$, $CO_2R^d$, $SO_2R^d$, or $SO_2NR^bR^c$; wherein the alkyl, cycloalkyl, or heterocycloalkyl is unsubstituted or substituted with 1 to 3 $R^{5b}$;

$R^{5b}$ is selected from H, D, halogen, cyano, $OR^a$, $SR^a$, $NR^bR^c$, $COR^d$, $CONR^bR^c$, $CO_2R^d$, $SO_2R^d$, or $SO_2NR^bR^c$;

$R^8$ is selected from H, D, alkyl, halogen, haloalkyl, or $OR^a$;

$R^a$, $R^b$, $R^c$, and $R^d$ are each selected from H, D, alkyl, alkenyl, alkynyl, cycloalkyl, heterocycloalkyl, aryl, or heteroaryl, wherein the alkyl, alkenyl, alkynyl, cycloalkyl, heterocycloalkyl, aryl, or heteroaryl is unsubstituted or substituted with 1 to 4 $R^6$;

$R^6$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl;

wherein $R^b$ and $R^c$ in a group containing both $R^b$ and $R^c$ are attached to a N atom in the group by a single bond or form a heterocycloalkyl together with the N atom to which they are attached, and the heterocycloalkyl is unsubstituted or substituted with 1 to 3 $R^7$;

$R^7$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl; and z is 1 or 2.

DETAILED DESCRIPTION

The term "halo" or "halogen" in the present application includes fluorine, chlorine, bromine, and iodine.

The term "alkyl" refers to a straight- or branched-chain saturated hydrocarbon group. Examples of alkyl groups include methyl (Me), ethyl (Et), propyl (such as n-propyl and isopropyl), butyl (such as n-butyl, isobutyl, and t-butyl), pentyl (such as n-pentyl, isopentyl, and neopentyl), hexyl (such as n-hexyl, 2-hexyl, 3-hexyl, 2-methylpentyl, 3-methylpentyl, 2,2-dimethylbutyl, and 3-ethylpentyl-1), heptyl (such as n-heptyl, 2-heptyl, 3-heptyl, 4-heptyl, 2-methylhexyl, 3-methylhexyl, 2,2-dimethylpentyl, 3,3-dimethylpentyl, and 3-ethylpentyl-1), octyl (such as 1-octyl, 2-octyl, and 2-ethylhexyl), nonyl (such as 1-nonyl), decyl (such as n-decyl), and similar groups. In particular, alkyl refers to straight- or branched-chain alkyl having 1, 2, 3, 4, 5, 6, 7, 8, 9, 10, 11, 12, 13, 14, 15, 16, 17, 18, 19, or 20 carbon stoms, more specifically refers to straight- or branched-chain alkyl having 1, 2, 3, 4, 5, 6, 7, 8, 9, or 10 atoms, and more preferably refers to straight- or branched-chain alkyl having 1, 2, 3, 4, 5, or 6 atoms. Unless defined to the contrary, all groups in the present application are defined as defined herein.

The term "haloalkyl" refers to an alkyl group having one or more halogen substituents. The alkyl group and the halo or halogen are as defined above. Examples of haloalkyl groups include $CH_2F$, $CHF_2$, $CF_3$, $C_2F_5$, $CCl_3$, and similar groups The term "alkenyl" refers to a hydrocarbon group having one or more C=C double bonds. Examples of alkenyl groups include vinyl, propenyl, allyl, 1-butenyl, 2-butenyl, 1,3-butadienyl, 1-pentenyl, 2-pentenyl, 1,3-pentadienyl, 1-hexenyl, 2-hexenyl, and similar groups.

The term "alkynyl" refers to a hydrocarbon group having one or more C=C triple bonds. Examples of alkynyl groups include ethynyl, propynyl, propargyl, 1-butynyl, 2-butynyl, 1-pentynyl, 2-pentynyl, 1-hexynyl, 2-hexynyl, and similar groups.

The term "cycloalkyl" refers to a non-aromatic carbocyclic ring and includes cyclized alkyl, cyclized alkenyl, and cyclized alkynyl groups. Cycloalkyl groups may be a monocyclic or polycyclic (for example, with 2, 3, or 4 fused rings) ring system, including spirocyclic rings. In some embodiments, a cycloalkyl group may have 3, 4, 5, 6, 7, 8, 9, 10, 11, 12, 13, 14, 15, 16, 17, 18, 19, or 20 carbon atoms. The cycloalkyl group may further have 0, 1, 2, or 3 C=C double bonds and/or 0, 1, or 2 C=C triple bonds. Also included in the definition of cycloalkyl are moieties having one or more aromatic rings fused to (for example, having a common bond with) the cycloalkyl ring, such as benzo derivatives of pentane, pentene, hexane, and hexane, and similar compounds. A cycloalkyl group having one or more fused aromatic rings may be attached through the aromatic part or the non-aromatic part. Examples of cycloalkyl groups include cyclopropyl, cyclobutyl, cyclopentyl, cyclohexyl, cycloheptyl, cyclopentenyl, cyclohexenyl, cyclohexadienyl, cycloheptenyl, cycloheptadienyl, adamantyl, dihydroindenyl, tetrahydronaphthyl, and similar groups.

The term "heterocycloalkyl" refers to a non-aromatic heterocyclic ring in which one or more atoms forming the ring are hetero atoms such as O, N, P or S. Heterocycloalkyl groups may include a monocyclic or polycyclic (for example, with 2, 3, or 4 fused rings) ring system and spirocyclic rings. Examples of preferred "heterocycloalkyl" groups include, but are not limited to, aziridinyl, azetidinyl, tetrahydrofuranyl, tetrahydrothienyl, pyrrolidinyl, oxazolidinyl, thiazolidinyl, imidazolidinyl, isoxazolidinyl, isothiazolidinyl, pyrazolidinyl, morpholinyl, thiomorpholinyl, piperazinyl, piperidinyl, and similar groups. Also included in the definition of heterocycloalkyl are moieties having one or more aromatic rings fused to (for example, having a common bond with) the non-aromatic heterocycloalkyl ring, such as 2,3-dihydrobenzofuranyl, 1,3-benzodioxolenyl, benzo-1,4-dioxanyl, phthalimidyl, naphthalimidyl, and similar groups. A heterocycloalkyl group having one or more fused aromatic rings may be attached through the aromatic part or the non-aromatic part.

The term "aryl" refers to a monocyclic or polycyclic (for example, with 2, 3 or 4 fused rings) aromatic hydrocarbon group, such as phenyl, naphthyl, anthracenyl, phenanthryl, indenyl, and similar groups.

The term "heteroaryl" refers to an aromatic heterocyclic ring having at least one heteroatom such as O, N, or S. Heteroaryl groups include a monocyclic or polycyclic (for example, with 2, 3, or 4 fused rings) ring system. Any N atom forming a ring in the heterocyclic group may be oxidized to form an N-oxide. Examples of preferred "heteroaryl" groups include, but are not limited to, pyridyl, pyrimidinyl, pyrazinyl, pyridazinyl, triazinyl, furyl, thienyl, imidazolyl, triazolyl, tetrazolyl, thiazolyl, isothiazolyl, 1,2,4-thiadiazolyl, pyrrolyl, pyrazolyl, oxazolyl, isoxazolyl, oxadiazolyl, benzofuranyl, benzothienyl, benzothiazolyl, indolyl, indazolyl, quinolinyl, isoquinolinyl, purinyl, carbazolyl, benzimidazolyl, pyrrolopyridyl, pyrrolopyrimidinyl, pyrazolopyridyl, pyrazolopyrimidinyl, and similar groups.

The term "compound", as used herein, is meant to include all stereoisomers, geometric isomers, tautomers, and isotopes.

The compound of the present application may be asymmetric, for example, having one or more stereocenters. Unless otherwise defined, all stereoisomers may be enantiomers and diastereomers. The compound of the present application that contains asymmetrically substituted carbon atoms may be separated into an optically pure form or a racemic form. The optically pure form may be prepared by resolution of a racemate or by using a chiral synthon or a chiral reagent.

The compound of the present application may also include tautomers. The tautomers are produced by exchanging a single bond with an adjacent double bond together with the migration of a proton.

The compound of the present application may also include all isotopic forms of atoms present in intermediates or final compounds. The isotopes include those atoms that have the same atomic number but different masses. For example, the isotopes of hydrogen include deuterium and tritium.

The present application further includes pharmaceutically acceptable salts of compounds represented by Formula (I) and Formula (IA). The pharmaceutically acceptable salt refers to a derivative of a compound modified through the conversion of a parent compound into its salt form through the present base part or a compound modified through the conversion of a parent compound into its salt form through the present acid part. Examples of pharmaceutically acceptable salts include, but are not limited to, salts of inorganic or organic acids of basic groups (such as ammonia) or salts of inorganic or organic bases of acid groups (such as carboxylic acid). The pharmaceutically acceptable salt of the present application may be synthesized by reacting the free base forms of the parent compounds represented by Formula (I) and formula (IA) with an appropriate acid in 1 to 4 in a solvent system. Appropriate salts are listed in *Remington's Pharmaceutical Sciences*, 17th ed., Mack Publishing Company, Easton, Pa., 1985, p. 1418 and *Journal of Pharmaceutical Science*, 66, 2 (1977).

The compound and the pharmaceutically acceptable salt thereof in the present application further include solvate forms or hydrate forms. Generally speaking, the solvate forms or the hydrate forms are equivalent to non-solvate forms or non-hydrate forms, both of which are included in the scope of the present application. Some compounds of the present application may exist in a polycrystalline form or an amorphous form. In general, all physical forms of the compounds are included in the scope of the present application.

The present application further includes prodrugs of the compounds represented by Formula (I) and Formula (IA). A prodrug is a pharmacological substance (that is, a drug) derived from a parent drug. Once administered, the prodrug is metabolized in a body into the parent drug. The prodrug may be prepared by substituting one or more functional groups present in the compound. The preparation and use of the prodrug may be found in T. Higuchi and V. Stella, *Pro-drugs as Novel Delivery Systems*, Vol. 14 of the A.C.S. Symposium Series and Bioreversible Carriers in Drug Design, ed. Edward B. Roche, American Pharmaceutical Association and Pergamon Press, 1987.

In some embodiments, the compound of the present application is selected from the following compounds:

N-(1-(1-(1-acetylpiperidin-4-yl)azetidin-3-yl)-3-(difluoromethyl)-1H-pyrazol-4-yl)-6-(1-(2,2-difluoroethyl)-1H-pyrazol-4-yl)-2-picolinamide 6-(1-(2,2-difluoroethyl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(2,2,2-trifluoroethyl)-1H-pyrazol-4-yl)-2-picolinamide N-(3-(difluoromethyl)-1-(1-(1-(2-hydroxyacetyl)piperidin-4-yl)azetidin-3-yl)-1H-pyrazol-4-yl)-6-(1-(2,2,2-trifluoroethyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(difluoromethyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-methyl-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-ethyl-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-isopropyl-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(1-cyanocyclopropyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(1-cyanocyclobutyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(1-(aminomethyl)cyclobutyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(2-cyanopropan-2-yl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(1-amino-2-methylpropan-2-yl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(1-(hydroxymethyl)cyclobutyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(2-hydroxy-2-methylpropyl)-1H-pyrazol-4-yl)-2-picolinamide N-(1-(1-(1-acetylpiperidin-4-yl)azetidin-3-yl)-3-(difluoromethyl)-1H-pyrazol-4-yl)-6-(1-(1-hydroxy-2-methylpropyl-2-yl)-1H-pyrazol-4-yl)-2-picolinamide 6-(1-(1-amino-2-methylpropan-2-yl)-1H-pyrazol-4-yl)-N-(3-(difluoromethyl)-1-(1-(1-(dimethylcarbamoyl)piperidin-4-yl)azetidin-3-yl)-1H-pyrazol-4-yl)-2-picolinamide methyl 4-(3-(4-(6-(1-(1-amino-2-methylpropan-2-yl)-1H-pyrazol-4-yl)-2-picolinamide)-3-(difluoromethyl)-1H-pyrazol-1-yl)azetidin-1-yl)piperidine-1-carboxylate N-(1-(1-(1-acetylpiperidin-4-yl)azetidin-3-yl)-3-(difluoromethyl)-1H-pyrazol-4-yl)-6-(1H-pyrazol-4-yl)-2-picolinamide N-(3-(difluoromethyl)-1-(1-(1-(dimethylcarbamoyl)piperidin-4-yl)azetidin-3-yl)-1H-pyrazol-4-yl)-6-(1H-pyrazol-4-yl)-2-picolinamide methyl 4-(3-(4-(6-(1H-pyrazol-4-yl)-2-picolinamide)-3-(difluoromethyl)-1H-pyrazol-1-yl)azetidin-1-yl)piperidine-1-carboxylate N-(1-(1-(1-acryloylpiperidin-4-yl)azetidin-3-yl)-3-(difluoromethyl)-1H-pyrazol-4-yl)-6-(1H-pyrazol-4-yl)-2-picolinamide N-(1-(1-(1-acryloylpiperidin-4-yl)azetidin-3-yl)-3-(difluoromethyl)-1H-pyrazol-4-yl)-6-(1H-pyrazol-3-yl)-2-picolinamide N-(1-(1-(1-acetylpiperidin-4-yl)azetidin-3-yl)-3-(difluoromethyl)-1H-pyrazol-4-yl)-6-(1H-pyrazol-3-yl)-2-picolinamide methyl 4-(3-(4-(6-(1H-pyrazol-3-yl)-2-picolinamide)-3-(difluoromethyl)-1H-pyrazol-1-yl)azetidin-1-yl)piperidine-1-carboxylate N-(3-(difluoromethyl)-1-(1-(1-propionylpiperidin-4-yl)azetidin-3-yl)-1H-pyrazol-4-yl)-6-(1H-pyrazol-3-yl)-2-picolinamide N-(3-(difluoromethyl)-1-(1-(1-(2-hydroxyacetyl)piperidin-4-yl)azetidin-3-yl)-1H-pyrazol-4-yl)-6-(1H-pyrazol-3-yl)-2-picolinamide N-(3-(difluoromethyl)-1-(1-(1-(dimethylcarbamoyl)piperidin-4-yl)azetidin-3-yl)-1H-pyrazol-4-yl)-6-(1H-pyrazol-3-yl)-2-picolinamide N-(3-(difluoromethyl)-1-(1-(1-isobutyrylpiperidin-4-yl)azetidin-3-yl)-1H-pyrazol-4-yl)-6-(1H-pyrazol-3-yl)-2-picolinamide (S)—N-(3-(difluoromethyl)-1-(1-(1-(2-hydroxypropionyl)piperidin-4-yl)azetidin-3-yl)-1H-pyrazol-4-yl)-6-(1-(2,2,2-trifluoroethyl)-1H-pyrazol-4-yl)-2-picolinamide (R)—N-(3-(difluoromethyl)-1-(1-(1-(2-hydroxypropionyl)piperidin-4-yl)azetidin-3-yl)-1H-pyrazol-4-yl)-6-(1-(2,2,2-trifluoroethyl)-1H-pyrazol-4-yl)-2-picolinamide N-(3-(difluoromethyl)-1-(1-(1-(2-hydroxy-2-methylpropionyl)piperidin-4-yl)azetidin-3-yl)-1H-pyrazol-4-yl)-6-(1-(2,2,2-trifluoroethyl)-1H-pyrazol-4-yl)-2-picolinamide N-(3-(difluoromethyl)-1-(1-(1-(methylsulfonyl)piperidin-4-yl)azetidin-3-yl)-1H-pyrazol-4-yl)-6-(1-(2,2,2-trifluoroethyl)-1H-pyrazol-4-yl)-2-picolinamide (S)-6-(1-(2,2-difluoroethyl)-1H-pyrazol-4-yl)-N-(3-(difluoromethyl)-1-(1-(1-(2-hydroxypropionyl)piperidin-4-yl)azetidin-3-yl)-1H-pyrazol-4-yl)-2-picolinamide (R)-6-(1-(2,2-difluoroethyl)-1H-pyrazol-4-yl)-N-(3-(difluoromethyl)-1-(1-(1-(2-hydroxypropionyl)piperidin-4-yl)azetidin-3-yl)-1H-pyrazol-4-yl)-2-picolinamide 6-(1-(2,2-difluoroethyl)-1H-pyrazol-4-yl)-N-(3-(difluoromethyl)-1-(1-(1-(2-hydroxy-2-methylpropionyl)piperidin-4-yl)azetidin-3-yl)-1H-pyrazol-4-yl)-2-picolinamide 6-(1-(2,2-difluoroethyl)-1H-pyrazol-4-yl)-N-(3-(difluoromethyl)-1-(1-(1-(methylsulfonyl)piperidin-4-yl)azetidin-3-yl)-1H-pyrazol-4-yl)-2-picolinamide 6-(1-(2,2-difluoroethyl)-1H-pyrazol-4-yl)-N-(3-(difluoromethyl)-1-(1-(1-(dimethylcarbamoyl)piperidin-4-yl)azetidin-3-yl)-1H-pyrazol-4-yl)-2-picolinamide (S)—N-(3-(difluoromethyl)-1-(1-(1-(2-hydroxypropionyl)piperidin-4-yl)azetidin-3-yl)-1H-pyrazol-4-yl)-6-(1H-pyrazol-3-yl)-2-picolinamide (R)—N-(3-(difluoromethyl)-1-(1-(1-(2-hydroxypropionyl)piperidin-4-yl)azetidin-3-yl)-1H-pyrazol-4-yl)-6-(1H-pyrazol-3-yl)-2-picolinamide N-(3-(difluoromethyl)-1-(1-(1-(2-hydroxy-2-methylpropionyl)piperidin-4-yl)azetidin-3-yl)-1H-pyrazol-4-yl)-6-(1H-pyrazol-3-yl)-2-picolinamide N-(3-(difluoromethyl)-1-(1-(1-(methylsulfonyl)piperidin-4-yl)azetidin-3-yl)-1H-pyrazol-4-yl)-6-(1H-pyrazol-3-yl)-2-picolinamide 6-(1-(2-cyanopropan-2-yl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide.

In another aspect of the present application, a composition is further provided. The composition consists of the compound represented by Formula (I) and Formula (IA), a N-oxide derivative thereof, an individual isomer thereof, or a mixture of isomers thereof, a pharmaceutically acceptable salt, and a pharmaceutically acceptable carrier or excipient. The composition of the present application may be administered through oral administration, parenteral administration (injection administration), spray inhalation, topical administration, rectal administration, nasal administration, vaginal administration, intraperitoneal administration, or via an implanted reservoir.

In another aspect of the present application, the present application provides a use of the compound represented by Formula (I) and Formula (IA) and a pharmaceutically acceptable salt for inhibiting protein kinases.

In some embodiments, the protein kinases are IRAK family kinases, especially IRAK4 kinase.

In another aspect of the present application, the present application provides a use of the compound represented by Formula (I) and Formula (IA) and a pharmaceutically acceptable salt for treating a disease caused by protein kinases.

In some embodiments, the compound or the composition of the present application may be used for treating autoimmune diseases; inflammatory diseases; pain disorders; respiratory tract, airway and lung diseases; lung inflammation and injury; pulmonary hypertension; gastrointestinal diseases; allergic diseases; infectious diseases; trauma disorders and tissue injuries; fibrotic diseases; eye diseases; joint, muscle and bone diseases; skin diseases; kidney diseases; hematopoietic diseases; liver diseases; oral diseases; metabolic disorders and heart diseases; vascular diseases; neuroinflammatory diseases; neurodegenerative diseases; sepsis; and genetic disorders; which are caused by the IRAK family kinases, especially IRAK4 kinase.

In some embodiments, the autoimmune diseases and the inflammatory diseases in the present application are selected from systemic lupus erythematosus (SLE), lupus nephritis, arthritis, psoriasis, colitis, Crohn's disease, atopic dermatitis, liver fibrosis, Alzheimer's disease, gout, cryopyrin-associated periodic syndrome (CAPS), chronic kidney disease or acute kidney injury, chronic obstructive pulmonary disease (COPD), asthma, bronchi spasms, and graft-versus-host disease.

In some embodiments, the compound or the composition of the present application may be used for treating abnormal cell proliferation diseases, especially cancer, caused by the IRAK family kinases, especially IRAK4 kinase.

In some embodiments, the cancer in the present application includes breast cancer, small cell lung cancer, non-small cell lung cancer, bronchi alveolar cancer, prostate cancer, cholangiocarcinoma, bone cancer, bladder cancer, head and neck cancer, renal cancer, liver cancer, gastrointestinal tissue cancer, esophageal cancer, ovarian cancer, pancreatic cancer, skin cancer, testicular cancer, thyroid cancer, uterine cancer, cervical and vaginal cancer, leukemia, multiple myeloma, and lymphoma.

In another aspect of the present application, the compound represented by Formula (I) and Formula (IA) and a pharmaceutically acceptable salt of the present application may be used in combination with one or more other medicaments. The compound of the present application and the medicaments used in combination with the compound may achieve an additive or synergistic effect when they are used in combination. The medicaments used in combination with the compound may be a small molecule medicament, a monoclonal antibody medicament, a fusion protein medicament, or an anti-sense DNA medicament.

In another aspect of the present application, a method for preparing the compound represented by Formula (I) or the pharmaceutically acceptable salt thereof described above is provided. The method includes the following steps:

A. reacting a nitro pyrazole carboxylic acid ester A-1 with a Boc-protected azetidine sulfonate A-2 to give A-3, wherein $R^1$ is alkyl and $R^2$ is alkyl or aryl;

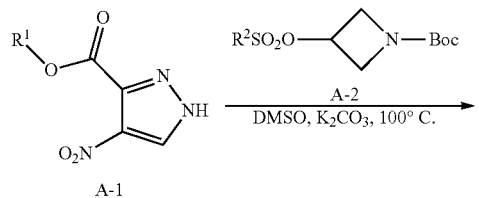

A-1

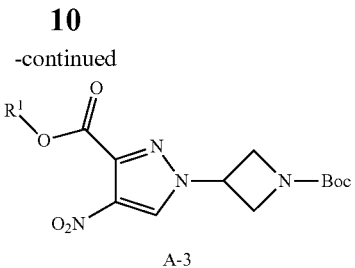

A-3

B. reducing the carboxylic acid ester in A-3 with a reducing agent such as diisobutylaluminum hydride (DIBAL-H) to give an aldehyde B-1;

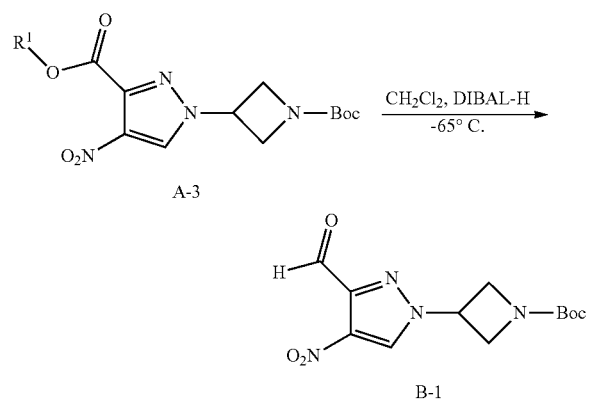

C. converting the aldehyde group in B-1 to a difluoromethyl group with a fluorine reagent such as diethylaminosulfur trifluoride (DAST) to give C-1;

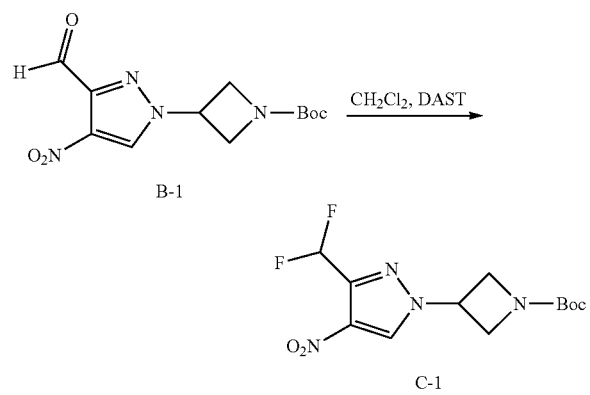

D. removing Boc in C-1 with an acid such as trifluoroacetic acid and performing reductive amination with Boc-protected piperidone to give D-1;

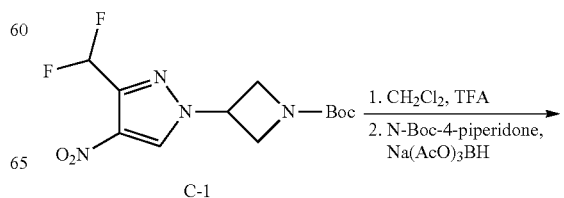

-continued

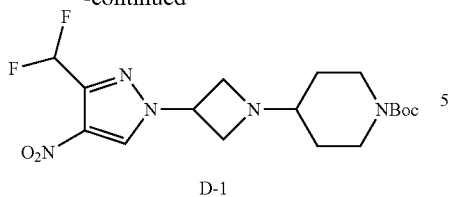
D-1

E. removing Boc in D-1 with an acid such as trifluoroacetic acid, and condensing D-1 and an acid chloride, or condensing D-1 and an acid with a condensing agent such as HATU, to give E-1, wherein L is chlorine or OH;

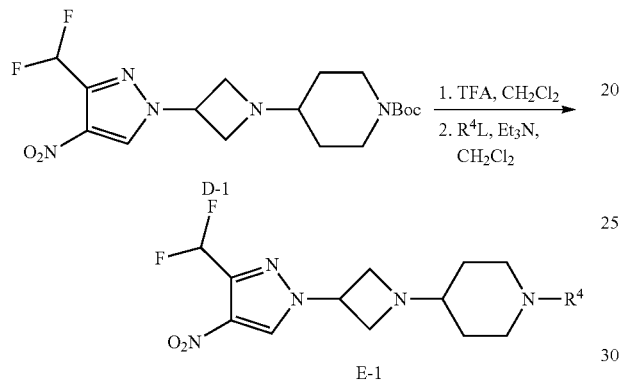

F. reducing the nitro group in E-1 with a reducing agent such as H₂ and Pd/C to give an amino compound F-1;

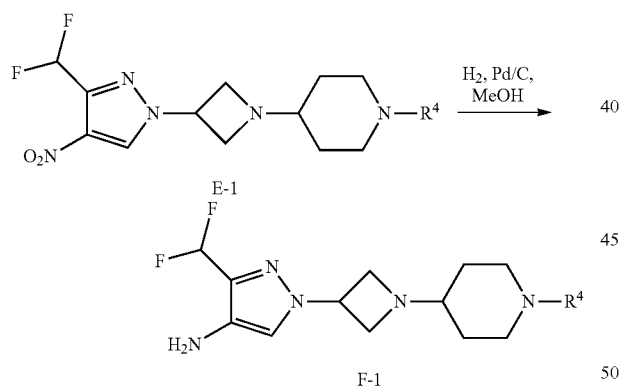

G. coupling a pyrazole boronic acid ester G-1 and 6-bromo-2-pyridinecarboxylic acid (X=H) or 6-bromo-2-pyridinecarboxylic acid ester (X=alkyl) G-2 with a palladium catalyst such as Pd(PPh₃)₄, followed by hydrolysis with a base such as NaOH (when X=alkyl), to give G-3;

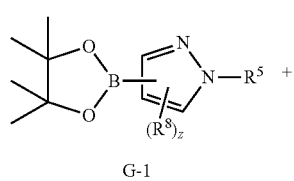
G-1

-continued

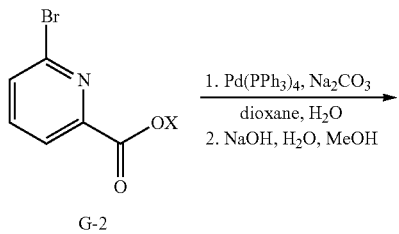
G-2

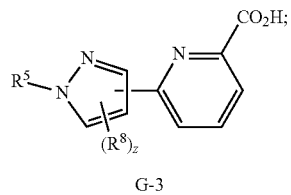
G-3

H. condensing the carboxylic acid G-3 and the amino intermediate F-1 with a condensing agent such as HATU to give a compound IA of the present application; wherein if R⁵ in IA contains an amino group, then reducing the cyano group in R⁵ with a reducing agent such as NaBH₄/CoCl₂/MeOH after condensation of G-3 and F-1. to give a compound IA with R⁵ containing amino;

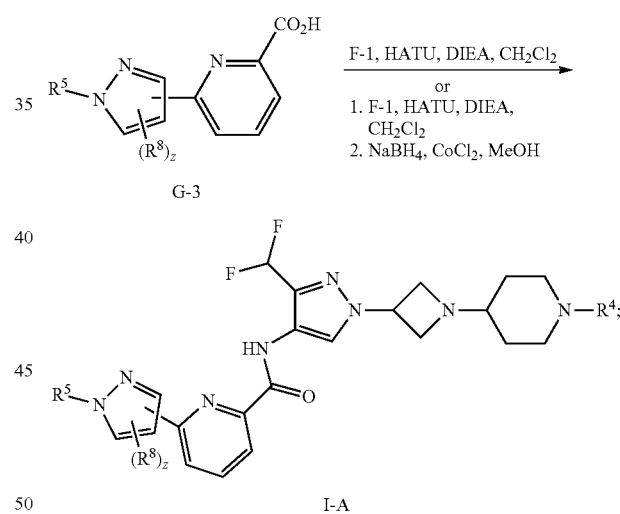
I-A

I. condensing the amino intermediate F-1 and a pyridine carboxylic acid G-2 with a condensing agent such as HATU to give I-1, and coupling I-1 and a boronic acid ester G-1 with a palladium catalyst such as Pd(PPh₃)₄ to give a compound IA of the present application

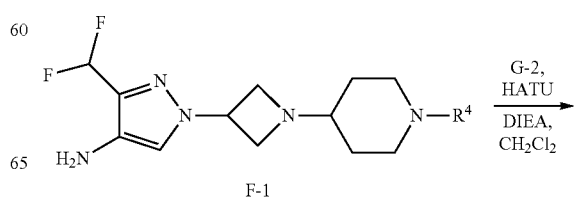
F-1

-continued

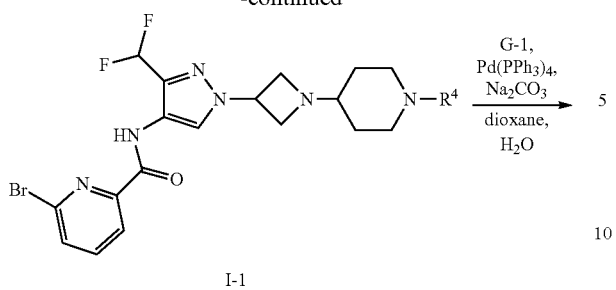

I-1

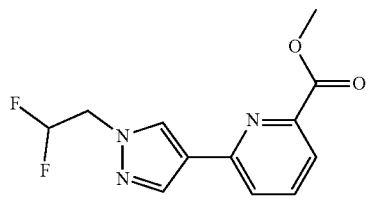

Step 2. Methyl 6-(1-(2,2-difluoroethyl)-1H-pyrazol-4-yl)-2-picolinate

Under the protection of nitrogen, 1-(2,2-difluoroethyl)-4-iodo-1H-pyrazole (2.0 g, 7.8 mmol), bis(pinacolato)diboron (4.0 g, 15.6 mmol), Pd(dppf)Cl$_2$ (571 mg, 0.78 mmol), AcOK (2.3 g, 23.4 mmol), and dioxane (40 mL) were added in a 100 mL round-bottom flask, heated to 100° C., and reacted for 2 h. After the reaction was completed, the solution was filtered and the filter residues were washed with EtOAc. The filtrate was added with H$_2$O and extracted with EtOAc. The organic phases were combined, washed with a saturated NaCl solution, dried over anhydrous Na$_2$SO$_4$, filtered, and concentrated. The obtained residues were directly used in the next step.

Under the protection of nitrogen, the residues obtained above, methyl 6-bromo-2-picolinate (1.7 g, 7.8 mmol), Pd(PPh$_3$)$_4$ (901 mg, 0.78 mmol), Na$_2$CO$_3$ (1.7 g, 15.6 mmol), dioxane (40 mL), and H$_2$O (8 mL) were added in a 100 mL round-bottom flask, heated to 80° C., and reacted for 2 h. After the reaction was completed, the solution was filtered and the filter residues were washed with EtOAc. The filtrate was added with H$_2$O and extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=1:1) to give 1.3 g of product with a yield of 62%. LCMS (ESI): m/z=268 (M+H)$^+$.

I-A

Example 1

N-(1-(1-(1-acetylpiperidin-4-yl)azetidin-3-yl)-3-(difluoromethyl)-1H-pyrazol-4-yl)-6-(1-(2,2-difluoroethyl)-1H-pyrazol-4-yl)-2-picolinamide Step 1. 1-(2,2-Difluoroethyl)-4-iodo-1H-pyrazole

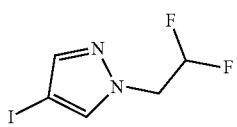

In a 100 mL round-bottom flask, 4-iodopyrazole (5.0 g, 25.7 mmol), triphenylphosphine (13.5 g, 51.4 mmol), and 2,2-difluoroethanol (2.1 g, 25.7 mmol) were dissolved in THF (80 mL). Activated 4A molecular sieve (10.0 g) and diisopropyl azodicarboxylate (DIAD) (10.4 g, 51.4 mmol) were added to the above solution and reacted at room temperature for 6 h. After the reaction was completed, the solution was diluted with water and extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=1:1) to give 4.6 g of product with a yield of 69%. LCMS (ESI): m/z=259 (M+H)$^+$.

Step 3. 6-(1-(2,2-Difluoroethyl)-1H-pyrazol-4-yl)-2-picolinic Acid

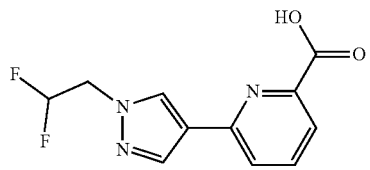 [SMILES: O=C(O)c1cccc(-c2cnn(CC(F)F)c2)n1]

Methyl 6-(1-(2,2-difluoroethyl)-1H-pyrazol-4-yl)-2-picolinate (1.3 g, 4.9 mmol) was dissolved in MeOH (15 mL), added with a solution of NaOH (1 M 15 mL), and reacted at room temperature for 1 h. After the reaction was completed, the solution was concentrated to remove MeOH, diluted with water, and extracted with EtOAc. The aqueous phase was adjusted with 4 M hydrochloric acid to a pH of 3. The solids were precipitated, filtered, and washed with H$_2$O to give 1.1 g of solids with a yield of 89%. LCMS (ESI): m/z=254 (M+H)$^+$.

Step 4. Ethyl 4-nitro-1H-pyrazole-3-carboxylate

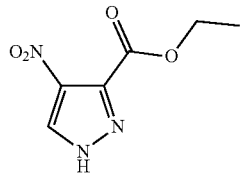

4-Nitro-1H-pyrazole-3-carboxylic acid (20.0 g, 127.4 mmol) was dissolved in EtOH (200 mL) and cooled in an ice bath. SOCl$_2$ (15 mL) was slowly added dropwise thereto and then heated to reflux for 6 h. After the reaction was completed, the solution was adjusted to be neutral with 5% Na$_2$CO$_3$ aqueous solution and distilled under reduced pressure to remove ethanol. The residues were diluted with water and extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 22.0 g of product with a yield of 93%. LCMS (ESI): m/z=186 (M+H)$^+$.

Step 5. T-butyl 3-(p-toluenesulfonyloxy)azetidine-1-carboxylate

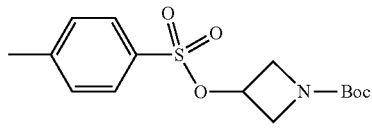 [SMILES: Cc1ccc(S(=O)(=O)OC2CN(C(=O)OC(C)(C)C)C2)cc1]

N-Boc-3-hydroxyazetidine (10 g, 57.8 mmol) was dissolved in CH$_2$Cl$_2$ (40 mL) in a 150 mL round-bottom flask and cooled in an ice bath. P-toluenesulfonyl chloride (11 g, 57.8 mmol) and pyridine (5.5 g, 69.4 mmol) were added to the above solution, then naturally warmed to room temperature, and reacted for 10 h. After the reaction was completed, the solution was diluted with water and layers were separated. The aqueous phase was extracted with CH$_2$Cl$_2$. The organic phases were combined, washed with 5% NaHCO$_3$ solution and a saturated NaCl solution in sequence, dried over anhydrous Na$_2$SO$_4$, filtered, and concentrated. The residues were purified through silica gel column chromatography (PE:EtOAc (v/v)=30:1) to give 13.5 g of product with a yield of 71%. LCMS (ESI): m/z=328 (M+H)$^+$.

Step 6. Ethyl 1-(1-(t-butylcarbonyl)azetidin-3-yl)-4-nitro-1H-pyrazole-3-carboxylate

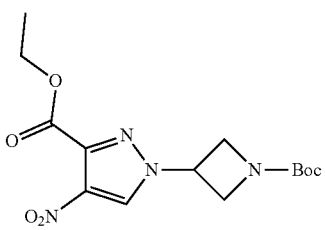 [SMILES: CCOC(=O)c1nn(C2CN(C(=O)OC(C)(C)C)C2)cc1[N+](=O)[O-]]

In a 500 mL three-necked round-bottom flask, ethyl 4-nitro-1H-pyrazole-3-carboxylate (22.0 g, 118.9 mmol), DMSO (200 mL), and K$_2$CO$_3$ (19.7 g, 142.7 mmol) were added, stirred at room temperature for 0.5 h, and then heated to 100° C. Then, a solution of t-butyl 3-(p-toluenesulfonyloxy)azetidine-1-carboxylate (38.9 g, 118.9 mmol) in DMSO (40 mL) was added dropwise to the above reaction solution and reacted for 6 h. After the reaction was completed, the solution was diluted with water and extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 20.5 g of product with a yield of 51%. LCMS (ESI): m/z=341 (M+H)$^+$.

Step 7. T-butyl 3-(3-formyl-4-nitro-1H-pyrazol-1-yl)azetidine-1-carboxylate

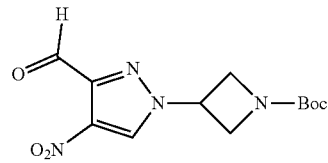

Under the protection of nitrogen, in a 500 mL three-necked round-bottom flask equipped with a thermometer, ethyl 1-(1-(t-butylcarbonyl)azetidin-3-yl)-4-nitro-1H-pyrazole-3-carboxylate (20.5 g, 60.3 mmol) was dissolved in CH$_2$Cl$_2$ (200 mL) and cooled in a dry ice/acetone bath. The internal temperature was kept below −65° C., a solution of 1 M DIBAL-H in n-hexane (150 mL) was slowly added dropwise into the above solution, and then the above reaction solution was poured into a saturated NH$_4$Cl solution (500 mL), stirred, and filtered. The filtrate was extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=2:1) to give 12.6 g of product with a yield of 71%. LCMS (ESI): m/z=315 (M+H$_2$O+H)$^+$.

Step 8. T-butyl 3-(3-(difluoromethyl)-4-nitro-1H-pyrazol-1-yl)azetidine-1-carboxylate

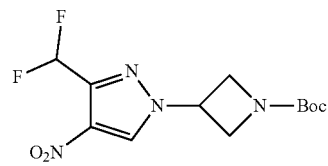

T-butyl 3-(3-formyl-4-nitro-1H-pyrazol-1-yl)azetidine-1-carboxylate (12.6 g, 42.6 mmol) was dissolved in CH$_2$Cl$_2$ (150 mL) in a 250 mL round-bottom flask and cooled in an ice bath. Diethylaminosulfur trifluoride (DAST) (17.1 g, 106.5 mmol) was slowly added dropwise thereto and reacted for 1 h with the temperature being maintained. After the reaction was completed, the solution was adjusted to be neutral with 5% NaHCO$_3$ aqueous solution and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 7.5 g of product with a yield of 55%. LCMS (ESI): m/z=319 (M+H)$^+$.

Step 9. t-butyl 4-(3-(3-(difluoromethyl)-4-nitro-1H-pyrazol-1-yl)azetidin-1-yl)piperidine-1-carboxylate

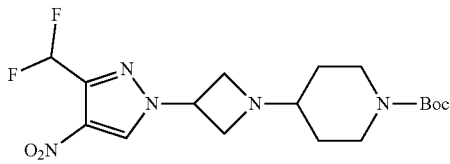

T-butyl 3-(3-(difluoromethyl)-4-nitro-1H-pyrazol-1-yl)azetidine-1-carboxylate (5.0 g, 15.7 mmol) was dissolved in CH$_2$Cl$_2$ (50 mL) in a 100 mL round-bottom flask, added with trifluoroacetic acid (10 mL), and reacted for 1 h at room temperature. After the reaction was completed, the solution was distilled under reduced pressure to remove the solvent and trifluoroacetic acid. The residues were dissolved in CH$_2$Cl$_2$ (50 mL) and adjusted with Et$_3$N to a pH of 8. N-Boc-4-piperidone (3.4 g, 17.3 mmol) and Na(AcO)$_3$BH (4.0 g, 18.8 mmol) were added to the above solution and reacted at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 5.5 g of product with a yield of 87%. LCMS (ESI): m/z=424 (M+Na)$^+$.

Step 10. 1-(4-(3-(3-(Difluoromethyl)-4-nitro-1H-pyrazol-1-yl)azetidin-1-yl)piperidin-1-yl) ethanone

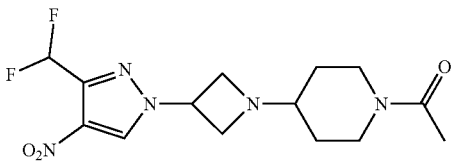

T-butyl 4-(3-(3-(difluoromethyl)-4-nitro-1H-pyrazol-1-yl)azetidin-1-yl)piperidine-1-carboxylate (5.5 g, 13.7 mmol) was dissolved in CH$_2$Cl$_2$ (50 mL) in a 100 mL round-bottom flask, added with trifluoroacetic acid (10 mL), and reacted for 1 h at room temperature. After the reaction was completed, the solution was distilled under reduced pressure to remove the solvent and trifluoroacetic acid. The residues were dissolved in CH$_2$Cl$_2$ (50 mL), added with Ac$_2$O (2.8 g, 27.4 mmol) and Et$_3$N (6 mL) in sequence, and reacted at room temperature for 0.5 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 4.1 g of product with a yield of 87%. LCMS (ESI): m/z=344 (M+H)$^+$.

Step 11. 1-(4-(3-(4-Amino-3-(difluoromethyl)-1H-pyrazol-1-yl)azetidin-1-yl)piperidin-1-yl)ethanone

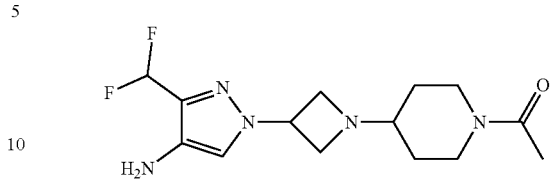

1-(4-(3-(3-(Difluoromethyl)-4-nitro-1H-pyrazol-1-yl)azetidin-1-yl)piperidin-1-yl)ethanone (4.1 g, 11.9 mmol) was dissolved in MeOH (50 mL) in a 100 mL round-bottom flask equipped with a hydrogen balloon, added with Pd/C (10% wet powder, 50 wt % moisture, 2.0 g), and stirred at room temperature for 2 h. After the reaction was completed, the solution was filtered and the filter residues were washed with MeOH. The filtrate was concentrated under reduced pressure to give 3.2 g of product which was directly used in the next step. LCMS (ESI): m/z=314 (M+H)$^+$.

Step 12. N-(1-(1-(1-acetylpiperidin-4-yl)azetidin-3-yl)-3-(difluoromethyl)-1H-pyrazol-4-yl)-6-(1-(2,2-difluoroethyl)-1H-pyrazol-4-yl)-2-picolinamide

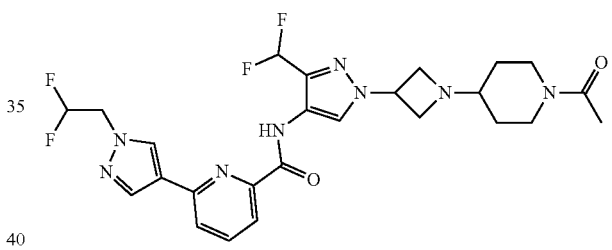

1-(4-(3-(4-Amino-3-(difluoromethyl)-1H-pyrazol-1-yl)azetidin-1-yl)piperidin-1-yl)ethanone (120 mg, 0.38 mmol), 6-(1-(2,2-difluoroethyl)-1H-pyrazol-4-yl)-2-picolinic acid (96 mg, 0.38 mmol), diisopropylethylamine (DIEA) (98 mg, 0.76 mmol), 2-(7-aza-1H-benzotriazol-1-yl)-1,1,3,3-tetramethylurea hexafluorophosphate (HATU) (175 mg, 0.46 mmol), and CH$_2$Cl$_2$ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (CH$_2$Cl$_2$:MeOH (v/v)=20:1) to give 126 mg of product with a yield of 61%. LCMS (ESI): m/z=549 (M+H)$^+$. $^1$H NMR (400 MHz, Chloroform-d) δ 10.47 (s, 1H), 8.49 (s, 1H), 8.10 (s, 1H), 8.07-8.02 (m, 2H), 7.88 (t, J=7.8 Hz, 1H), 7.64 (d, J=7.8 Hz, 1H), 6.88 (t, J=54.6 Hz, 1H), 6.15 (tt, J=55.4, 4.2 Hz, 1H), 5.00-4.90 (m, 1H), 4.55 (td, J=13.5, 4.2 Hz, 2H), 4.28-4.19 (m, 1H), 3.83 (t, J=7.6 Hz, 2H), 3.79-3.70 (m, 1H), 3.54-3.48 (m, 2H), 3.21-3.11 (m, 1H), 3.03-2.94 (m, 1H), 2.51-2.42 (m, 1H), 2.09 (s, 3H), 1.78-1.67 (m, 2H), 1.38-1.22 (m, 2H).

Example 2

6-(1-(2,2-Difluoroethyl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide Step 1. 1-(4-(3-(3-(Difluoromethyl)-4-nitro-1H-pyrazol-1-yl)azetidin-1-yl)piperidin-1-yl)-2-hydroxyethane-1-one

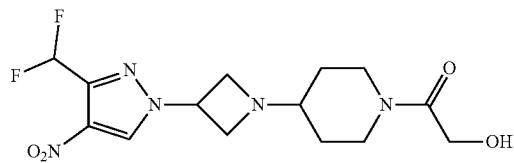 [SMILES: O=C(CO)N1CCC(N2CC(n3cc([N+](=O)[O-])c(C(F)F)n3)C2)CC1]

T-butyl 4-(3-(3-(difluoromethyl)-4-nitro-1H-pyrazol-1-yl)azetidin-1-yl)piperidine-1-carboxylate (1.0 g, 2.5 mmol) was dissolved in CH$_2$Cl$_2$ (10 mL) in a 50 mL round-bottom flask, added with trifluoroacetic acid (3 mL), and reacted for 1 h at room temperature. After the reaction was completed, the solution was distilled under reduced pressure to remove the solvent and trifluoroacetic acid. The residues were dissolved in CH$_2$Cl$_2$ (10 mL), added with hydroxyacetic acid (228 mg, 3.0 mmol), DIEA (645 mg, 5.0 mmol), and HATU (1.1 g, 3.0 mmol) in sequence, and reacted at room temperature for 0.5 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (PE:EtOAc (v/v)=1:1) to give 700 mg of product with a yield of 78%. LCMS (ESI): m/z=360 (M+H)$^+$.

Step 2. 1-(4-(3-(4-Amino-3-(difluoromethyl)-1H-pyrazol-1-yl)azetidin-1-yl)piperidin-1-yl)-2-hydroxyethane-1-one

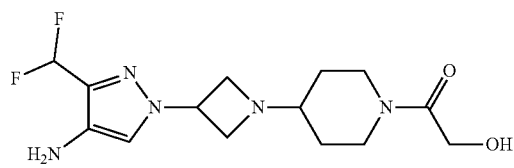 [SMILES: Nc1cn(C2CN(C3CCN(C(=O)CO)CC3)C2)nc1C(F)F]

1-(4-(3-(3-(Difluoromethyl)-4-nitro-1H-pyrazol-1-yl)azetidin-1-yl)piperidin-1-yl)-2-hydroxyethane-1-one (700 mg, 1.9 mmol) was dissolved in MeOH (10 mL) in a 25 mL round-bottom flask equipped with a hydrogen balloon, added with Pd/C (10% wet powder, 50 wt % moisture, 300 mg), and stirred at room temperature for 2 h. After the reaction was completed, the solution was filtered and the filter residues were washed with MeOH. The filtrate was concentrated under reduced pressure to give 580 mg of product which was directly used in the next step. LCMS (ESI): m/z=330 (M+H)$^+$.

Step 3. 6-(1-(2,2-difluoroethyl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide

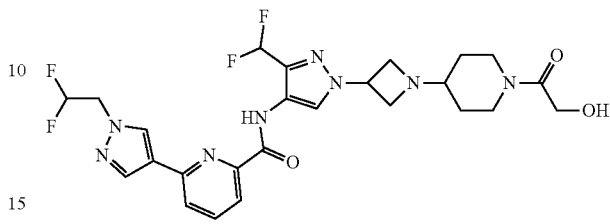

1-(4-(3-(4-Amino-3-(difluoromethyl)-1H-pyrazol-1-yl)azetidin-1-yl)piperidin-1-yl)-2-hydroxyethane-1-one (125 mg, 0.38 mmol), 6-(1-(2,2-difluoroethyl)-1H-pyrazol-4-yl)-2-picolinic acid (96 mg, 0.38 mmol), DIEA (98 mg, 0.76 mmol), HATU (175 mg, 0.46 mmol), and CH$_2$Cl$_2$ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (CH$_2$Cl$_2$:MeOH (v/v)=40:1) to give 145 mg of product with a yield of 68%. LCMS (ESI): m/z=565 (M+H)$^+$. $^1$H NMR (400 MHz, Chloroform-d) δ 10.48 (s, 1H), 8.50 (s, 1H), 8.11 (s, 1H), 8.08-8.03 (m, 2H), 7.89 (t, J=7.8 Hz, 1H), 7.64 (d, J=7.8 Hz, 1H), 6.89 (t, J=54.6 Hz, 1H), 6.16 (tt, J=55.4, 4.3 Hz, 1H), 5.00-4.91 (m, 1H), 4.56 (td, J=13.5, 4.3 Hz, 2H), 4.20-4.11 (m, 3H), 3.87-3.79 (m, 2H), 3.67 (s, 1H), 3.56-3.45 (m, 3H), 3.25-3.16 (m, 1H), 3.09-2.99 (m, 1H), 2.57-2.48 (m, 1H), 1.81-1.71 (m, 2H), 1.42-1.29 (m, 2H).

Example 3

N-(1-(1-(1-acetylpiperidin-4-yl)azetidin-3-yl)-3-(difluoromethyl)-1H-pyrazol-4-yl)-6-(1-(2,2,2-trifluoroethyl)-1H-pyrazol-4-yl)-2-picolinamide Step 1. 4-Iodo-1-(2,2,2-trifluoroethyl)-1H-pyrazole

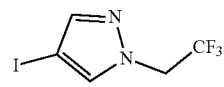

In a 150 mL round-bottom flask, 4-iodopyrazole (5.0 g, 25.7 mmol) was dissolved in DMF (50 mL), added with 2,2,2-trifluoroethyl trifluoromethanesulfonate (6.6 g, 28.3 mmol), and K$_2$CO$_3$ (7.1 g, 51.4 mmol), and then heated to 90° C. and reacted for 3 h. After the reaction was completed, the solution was diluted with water and layers were separated. The aqueous phase was extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=1:1) to give 4.3 g of product with a yield of 60%. LCMS (ESI): m/z=281 (M+H)$^+$.

Step 2. Methyl 6-(1-(2,2,2-trifluoromethyl)-1H-pyrazol-4-yl)-2-picolinate

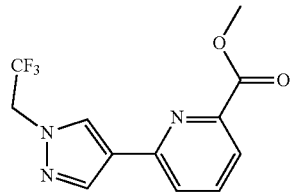 [SMILES: COC(=O)c1cccc(-c2cnn(CC(F)(F)F)c2)n1]

Under the protection of nitrogen, 4-iodo-1-(2,2,2-trifluoroethyl)-1H-pyrazole (4.3 g, 15.4 mmol), bis(pinacolato)diboron (7.8 g, 30.8 mmol), Pd(dppf)Cl₂ (1.1 g, 1.5 mmol), AcOK (4.5 g, 46.2 mmol), and dioxane (50 mL) were added in a 100 mL round-bottom flask, heated to 100° C., and reacted for 2 h. After the reaction was completed, the solution was filtered and the filter residues were washed with EtOAc. The filtrate was added with H₂O and extracted with EtOAc. The organic phases were combined, washed with a saturated NaCl solution, dried over anhydrous Na₂SO₄, filtered, and concentrated. The obtained residues were directly used in the next step.

Under the protection of nitrogen, the residues obtained above, methyl 6-bromo-2-picolinate (3.3 g, 15.4 mmol), Pd(PPh₃)₄ (1.7 g, 1.5 mmol), Na₂CO₃ (3.3 g, 30.8 mmol), dioxane (50 mL), and H₂O (10 mL) were added in a 100 mL round-bottom flask, heated to 80° C., and reacted for 2 h. After the reaction was completed, the solution was filtered and the filter residues were washed with EtOAc. The filtrate was added with H₂O and extracted with EtOAc. The organic phases were combined, washed with saturated NaCl solution, dried over anhydrous Na₂SO₄, filtered, and concentrated. The residues were purified through silica gel column chromatography (PE:EtOAc (v/v)=1:1) to give 3.1 g of product with a yield of 71%. LCMS (ESI): m/z=286 (M+H)⁺.

Step 3. 6-(1-(2,2,2-Trifluoromethyl)-1H-pyrazol-4-yl)-2-picolinic Acid

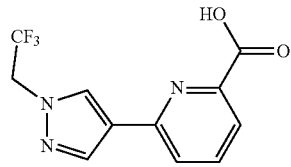 [SMILES: O=C(O)c1cccc(-c2cnn(CC(F)(F)F)c2)n1]

Methyl 6-(1-(2,2,2-trifluoromethyl)-1H-pyrazol-4-yl)-2-picolinate (3.1 g, 10.8 mmol) was dissolved in MeOH (30 mL), added with a solution of NaOH (1 M 30 mL), and reacted at room temperature for 1 h. After the reaction was completed, the solution was concentrated to remove MeOH, diluted with water, and extracted with EtOAc. The aqueous phase was adjusted with 4 M hydrochloric acid to a pH of 3. The solids were precipitated, filtered, and washed with H₂O to give 2.5 g of solids with a yield of 85%. LCMS (ESI): m/z=272 (M+H)⁺.

Step 4. N-(1-(1-(1-acetylpiperidin-4-yl)azetidin-3-yl)-3-(difluoromethyl)-1H-pyrazol-4-yl)-6-(1-(2,2,2-trifluoroethyl)-1H-pyrazol-4-yl)-2-picolinamide

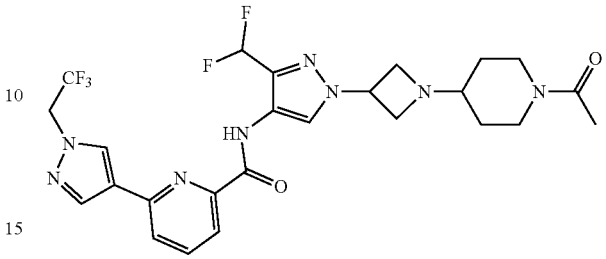

1-(4-(3-(4-Amino-3-(difluoromethyl)-1H-pyrazol-1-yl)azetidin-1-yl)piperidin-1-yl)ethanone (120 mg, 0.38 mmol), 6-(1-(2,2,2-trifluoromethyl)-1H-pyrazol-4-yl)-2-picolinic acid (103 mg, 0.38 mmol), DIEA (98 mg, 0.76 mmol), HATU (175 mg, 0.46 mmol), and CH₂Cl₂ (5 mL) were added in a 25 mL round-bottom flask and stirred at room temperature for 1 h. After the reaction was completed, the solution was diluted with water and extracted with CH₂Cl₂. The organic phases were combined, washed with a saturated NaCl solution, dried over anhydrous Na₂SO₄, filtered, and concentrated. The residues were purified through silica gel column chromatography (CH₂Cl₂:MeOH (v/v)=40:1) to give 190 mg of product with a yield of 88%. LCMS (ESI): m/z=567 (M+H)⁺. ¹H NMR (400 MHz, Chloroform-d) δ 10.47 (s, 1H), 8.50 (s, 1H), 8.12 (s, 1H), 8.11 (s, 1H), 8.06 (d, J=7.5 Hz, 1H), 7.90 (t, J=7.8 Hz, 1H), 7.66 (d, J=7.8 Hz, 1H), 6.88 (t, J=54.6 Hz, 1H), 5.00-4.90 (m, 1H), 4.80 (q, J=8.3 Hz, 2H), 4.28-4.19 (m, 1H), 3.83 (t, J=7.4 Hz, 2H), 3.79-3.71 (m, 1H), 3.51 (t, J=6.5 Hz, 2H), 3.21-3.11 (m, 1H), 3.04-2.94 (m, 1H), 2.52-2.42 (m, 1H), 2.09 (s, 3H), 1.80-1.69 (m, 2H), 1.39-1.22 (m, 2H).

Example 4

N-(3-(difluoromethyl)-1-(1-(1-(2-hydroxyacetyl)piperidin-4-yl)azetidin-3-yl)-1H-pyrazol-4-yl)-6-(1-(2,2,2-trifluoroethyl)-1H-pyrazol-4-yl)-2-picolinamide

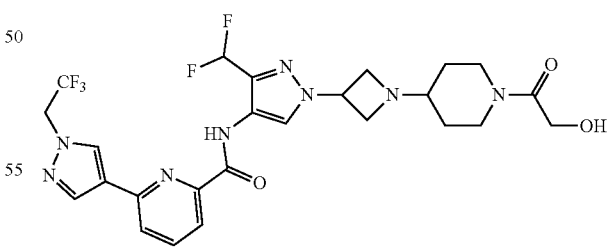

1-(4-(3-(4-Amino-3-(difluoromethyl)-1H-pyrazol-1-yl)azetidin-1-yl)piperidin-1-yl)-2-hydroxyethane-1-one (125 mg, 0.38 mmol), 6-(1-(2,2,2-trifluoroethyl)-1H-pyrazol-4-yl)-2-picolinic acid (103 mg, 0.38 mmol), DIEA (98 mg, 0.76 mmol), HATU (175 mg, 0.46 mmol), and CH₂Cl₂ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (CH$_2$Cl$_2$:MeOH (v/v)=40:1) to give 130 mg of product with a yield of 59%. LCMS (ESI): m/z=583 (M+H)$^+$. $^1$H NMR (400 MHz, Chloroform-d) δ 10.48 (s, 1H), 8.50 (s, 1H), 8.14-8.09 (m, 2H), 8.07 (d, J=7.6 Hz, 1H), 7.91 (t, J=7.7 Hz, 1H), 7.66 (d, J=7.8 Hz, 1H), 6.88 (t, J=54.5 Hz, 1H), 5.00-4.90 (m, 1H), 4.80 (q, J=8.3 Hz, 2H), 4.19-4.12 (m, 3H), 3.87-3.79 (m, 2H), 3.57-3.44 (m, 3H), 3.25-3.16 (m, 1H), 3.09-2.99 (m, 1H), 2.56-2.48 (m, 1H), 1.80-1.71 (m, 2H), 1.42-1.29 (m, 2H).

Example 5

N-(1-(1-(1-acetylpiperidin-4-yl)azetidin-3-yl)-3-(difluoromethyl)-1H-pyrazol-4-yl)-6-(1-(difluoromethyl)-1H-pyrazol-4-yl)-2-picolinamide Step 1. 1-(Difluoromethyl)-4-iodo-1H-pyrazole

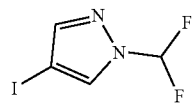

In a 150 mL round-bottom flask, 4-iodopyrazole (5.0 g, 25.7 mmol) was dissolved in DMF (50 mL), added with sodium 2-chloro-2,2-difluoroacetate (4.3 g, 28.3 mmol), and K$_2$CO$_3$ (7.1 g, 51.4 mmol), and then heated to 100° C. and reacted for 16 h. After the reaction was completed, the solution was diluted with water and layers were separated. The aqueous phase was extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 2.6 g of product with a yield of 41%. LCMS (ESI): m/z=245 (M+H)$^+$.

Step 2. Methyl 6-(1-(difluoromethyl)-1H-pyrazol-4-yl)-2-picolinate

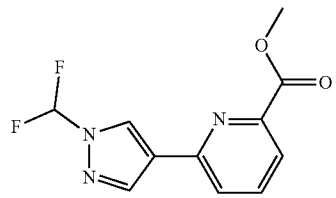 [SMILES: COC(=O)c1cccc(-c2cnn(C(F)F)c2)n1]

Under the protection of nitrogen, 1-(difluoromethyl)-4-iodo-1H-pyrazole (2.6 g, 10.6 mmol), bis(pinacolato)diboron (5.4 g, 21.2 mmol), Pd(dppf)Cl$_2$ (732 mg, 1.0 mmol), AcOK (3.1 g, 31.8 mmol), and dioxane (40 mL) were added in a 100 mL round-bottom flask, heated to 100° C., and reacted for 6 h. After the reaction was completed, the solution was filtered and the filter residues were washed with EtOAc. The filtrate was added with H$_2$O and extracted with EtOAc. The organic phases were combined, washed with a saturated Na$_2$SO$_4$, filtered, and concentrated. The obtained residues were directly used in the next step.

Under the protection of nitrogen, the residues obtained above, methyl 6-bromo-2-picolinate (2.3 g, 10.6 mmol), Pd(PPh$_3$)$_4$ (1.1 g, 1.0 mmol), Na$_2$CO$_3$ (2.2 g, 21.2 mmol), dioxane (40 mL), and H$_2$O (mL) were added in a 100 mL round-bottom flask, heated to 80° C., and reacted for 2 h. After the reaction was completed, the solution was filtered and the filter residues were washed with EtOAc. The filtrate was added with H$_2$O and extracted with EtOAc. The organic phases were combined, washed with saturated NaCl solution, dried over anhydrous Na$_2$SO$_4$, filtered, and concentrated. The residues were purified through silica gel column chromatography (PE:EtOAc (v/v)=1:1) to give 1.7 g of product with a yield of 63%. LCMS (ESI): m/z=254 (M+H)$^+$.

Step 3. 6-(1-(Difluoromethyl)-1H-pyrazol-4-yl)-2-picolinic Acid

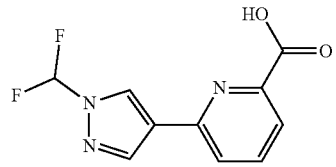 [SMILES: O=C(O)c1cccc(-c2cnn(C(F)F)c2)n1]

Methyl 6-(1-(difluoromethyl)-1H-pyrazol-4-yl)-2-picolinate (1.7 g, 6.7 mmol) was dissolved in MeOH (20 mL), added with a solution of NaOH (1 M 20 mL), and reacted at room temperature for 1 h. After the reaction was completed, the solution was concentrated to remove MeOH, diluted with water, and extracted with EtOAc. The aqueous phase was adjusted with 4 M hydrochloric acid to a pH of 3. The solids were precipitated, filtered, and washed with H$_2$O to give 1.1 g of solids with a yield of 69%. LCMS (ESI): m/z=240 (M+H)$^+$.

Step 4. N-(1-(1-(1-acetylpiperidin-4-yl)azetidin-3-yl)-3-(difluoromethyl)-1H-pyrazol-4-yl)-6-(1-(difluoromethyl)-1H-pyrazol-4-yl)-2-picolinamide

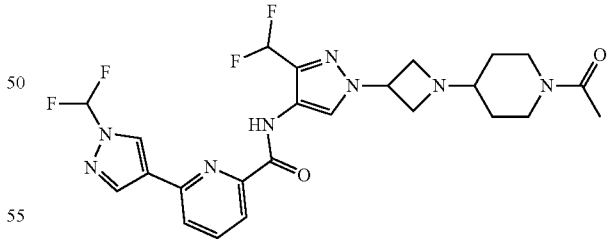

1-(4-(3-(4-Amino-3-(difluoromethyl)-1H-pyrazol-1-yl)azetidin-1-yl)piperidin-1-yl)ethanone (120 mg, 0.38 mmol), 6-(1-(difluoromethyl)-1H-pyrazol-4-yl)-2-picolinic acid (91 mg, 0.38 mmol), DIEA (98 mg, 0.76 mmol), HATU (175 mg, 0.46 mmol), and CH$_2$Cl$_2$ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated.

The residues were purified through silica gel column chromatography (CH₂Cl₂:MeOH (v/v)=40:1) to give 117 mg of product with a yield of 58%. LCMS (ESI): m/z=535 (M+H)⁺. ¹H NMR (400 MHz, Chloroform-d) δ 10.45 (s, 1H), 8.50 (s, 1H), 8.38 (s, 1H), 8.22 (s, 1H), 8.11 (d, J=7.5 Hz, 1H), 7.94 (t, J=7.8 Hz, 1H), 7.70 (d, J=7.8 Hz, 1H), 7.27 (d, J=60.3 Hz, 1H), 6.89 (t, J=54.6 Hz, 1H), 5.01-4.90 (m, 1H), 4.29-4.19 (m, 1H), 3.83 (t, J=7.5 Hz, 2H), 3.79-3.70 (m, 1H), 3.52 (t, J=6.6 Hz, 2H), 3.21-3.12 (m, 1H), 3.05-2.95 (m, 1H), 2.52-2.43 (m, 1H), 2.10 (s, 3H), 1.81-1.68 (m, 2H), 1.39-1.22 (m, 2H).

Example 6

N-(1-(1-(1-acetylpiperidin-4-yl)azetidin-3-yl)-3-(difluoromethyl)-1H-pyrazol-4-yl)-6-(1-methyl-1H-pyrazol-4-yl)-2-picolinamide

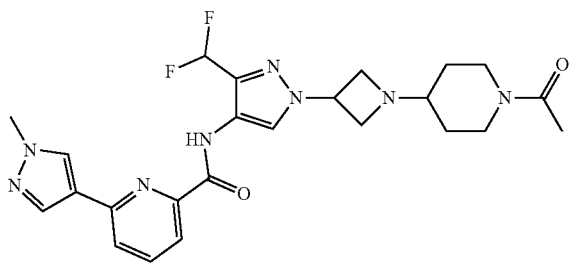 [SMILES: CC(=O)N1CCC(N2CC(n3cc(NC(=O)c4cccc(-c5cnn(C)c5)n4)c(C(F)F)n3)C2)CC1]

This example was prepared following the method of Example 5. LCMS (ESI): m/z=499 (M+H)⁺. ¹H NMR (400 MHz, Chloroform-d) δ 10.49 (s, 1H), 8.50 (s, 1H), 8.05-7.99 (m, 2H), 7.96 (s, 1H), 7.86 (t, J=7.8 Hz, 1H), 7.62 (d, J=7.8 Hz, 1H), 6.89 (t, J=54.6 Hz, 1H), 5.00-4.91 (m, 1H), 4.29-4.20 (m, 1H), 4.00 (s, 3H), 3.83 (t, J=7.6 Hz, 2H), 3.79-3.71 (m, 1H), 3.56-3.48 (m, 2H), 3.21-3.11 (m, 1H), 3.04-2.94 (m, 1H), 2.51-2.43 (m, 1H), 2.10 (s, 3H), 1.77-1.67 (m, 2H), 1.39-1.23 (m, 2H).

Example 7

N-(1-(1-(1-acetylpiperidin-4-yl)azetidin-3-yl)-3-(difluoromethyl)-1H-pyrazol-4-yl)-6-(1-ethyl-1H-pyrazol-4-yl)-2-picolinamide

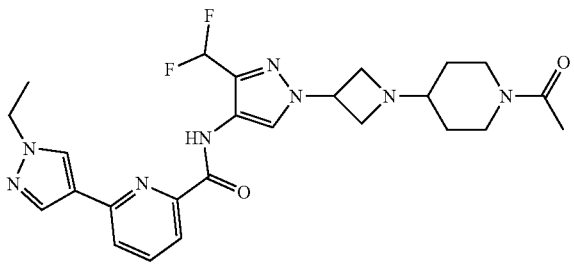 [SMILES: CCn1cc(-c2cccc(C(=O)Nc3cn(C4CN(C5CCN(C(C)=O)CC5)C4)nc3C(F)F)n2)cn1]

This example was prepared following the method of Example 5. LCMS (ESI): m/z=513 (M+H)⁺. ¹H NMR (400 MHz, Chloroform-d) δ 10.52 (s, 1H), 8.50 (s, 1H), 8.08-7.97 (m, 3H), 7.86 (t, J=7.7 Hz, 1H), 7.63 (d, J=7.8 Hz, 1H), 6.89 (t, J=54.6 Hz, 1H), 5.00-4.89 (m, 1H), 4.33-4.18 (m, 3H), 3.83 (t, J=7.5 Hz, 2H), 3.79-3.70 (m, 1H), 3.57-3.46 (m, 2H), 3.22-3.11 (m, 1H), 3.04-2.93 (m, 1H), 2.52-2.41 (m, 1H), 2.10 (s, 3H), 1.75-1.68 (m, 2H), 1.58 (t, J=7.4 Hz, 3H), 1.40-1.22 (m, 2H).

Example 8

N-(1-(1-(1-acetylpiperidin-4-yl)azetidin-3-yl)-3-(difluoromethyl)-1H-pyrazol-4-yl)-6-(1-isopropyl-1H-pyrazol-4-yl)-2-picolinamide

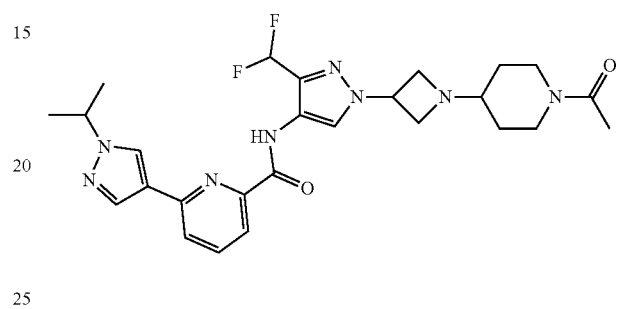

This example was prepared following the method of Example 5. LCMS (ESI): m/z=527 (M+H)⁺. ¹H NMR (400 MHz, Chloroform-d) δ 10.56 (s, 1H), 8.51 (s, 1H), 8.08 (s, 1H), 8.03 (s, 1H), 8.00 (d, J=7.8 Hz, 1H), 7.86 (t, J=7.8 Hz, 1H), 7.64 (d, J=7.8 Hz, 1H), 6.89 (t, J=54.6 Hz, 1H), 5.04-4.89 (m, 1H), 4.68-4.51 (m, 1H), 4.31-4.18 (m, 1H), 3.84 (t, J=7.5 Hz, 2H), 3.79-3.71 (m, 1H), 3.56-3.47 (m, 2H), 3.21-3.12 (m, 1H), 3.04-2.94 (m, 1H), 2.52-2.42 (m, 1H), 2.10 (s, 3H), 1.82-1.72 (m, 2H), 1.60 (d, J=6.7 Hz, 6H), 1.39-1.23 (m, 2H).

Example 9

N-(1-(1-(1-acetylpiperidin-4-yl)azetidin-3-yl)-3-(difluoromethyl)-1H-pyrazol-4-yl)-6-(1-(1-cyanocyclopropyl)-1H-pyrazol-4-yl)-2-picolinamide Step 1. 2-(4-Iodo-1H-pyrazol-1-yl)acetonitrile

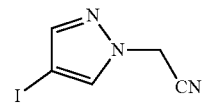

In a 250 mL round-bottom flask, 4-iodopyrazole (10.0 g, 51.5 mmol) was dissolved in DMF (100 mL), added with bromoacetonitrile (6.8 g, 56.6 mmol), and K₂CO₃ (14 g, 103.0 mmol), and then heated to 50° C. and reacted for 3 h. After the reaction was completed, the solution was diluted with water and layers were separated. The aqueous phase was extracted with EtOAc. The organic phases were combined, washed with a saturated NaCl solution, dried over anhydrous Na₂SO₄, filtered, and concentrated. The residues were purified through silica gel column chromatography (PE:EtOAc (v/v)=5:1) to give 11.2 g of product with a yield of 93%. LCMS (ESI): m/z=234 (M+H)⁺.

Step 2. 1-(4-Iodo-1H-pyrazol-1-yl)cyclopropane-1-carbonitrile

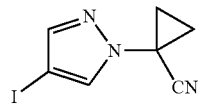

DMSO (50 mL) was added in a 150 mL round-bottom flask and cooled in an ice bath. Then NaH (3.4 g, 85.6 mmol, 60%) was added and stirred for 20 min. A mixed solution of 2-(4-iodo-1H-pyrazol-1-yl)acetonitrile (5.0 g, 21.4 mmol) and 1,2-dibromoethane (12.1 g, 64.2 mmol) in DMSO (10 mL) was added to the above reaction solution, naturally warmed to room temperature, and reacted for 8 h. After the reaction was completed, the above reaction solution was poured into an icy and saturated NH$_4$Cl aqueous solution, and the aqueous phase was extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=10:1) to give 1.8 g of product with a yield of 32%. LCMS (ESI): m/z=260 (M+H)$^+$.

Step 3. 6-(1-(1-Cyanocyclopropyl)-1H-pyrazol-4-yl)-2-picolinic Acid

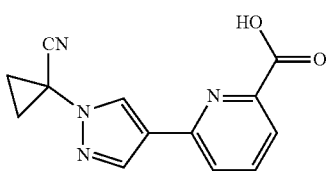 [SMILES: N#CC1(n2cc(-c3cccc(C(=O)O)n3)cn2)CC1]

Under the protection of nitrogen, 1-(4-iodo-1H-pyrazol-1-yl)cyclopropane-1-carbonitrile (1.8 g, 6.9 mmol), bis(pinacolato)diboron (3.5 g, 13.8 mmol), Pd(dppf)Cl$_2$ (0.5 g, 0.7 mmol), AcOK (2.0 g, 20.7 mmol), and DMF (30 mL) were added in a 100 mL round-bottom flask, heated to 100° C., and reacted for 2 h. After the reaction was completed, the solution was filtered and the filter residues were washed with EtOAc. The filtrate was added with H$_2$O and extracted with EtOAc. The organic phases were combined, washed with a saturated NaCl solution, dried over anhydrous Na$_2$SO$_4$, filtered, and concentrated. The obtained residues were directly used in the next step.

Under the protection of nitrogen, the residues obtained above, 6-bromo-2-picolinic acid (1.4 g, 6.9 mmol), Pd(PPh$_3$)$_4$ (0.8 g, 0.7 mmol), Na$_2$CO$_3$ (2.2 g, 20.7 mmol), dioxane (40 mL), and H$_2$O (10 mL) were added in a 100 mL round-bottom flask, heated to 80° C., and reacted for 10 h. After the reaction was completed, the solution was filtered and the filter residues were washed with EtOAc. The filtrate was added with H$_2$O and extracted with EtOAc. The aqueous phase was adjusted with 1 M HCl to a pH of 1, extracted with EtOAc, washed with a saturated NaCl solution, dried over anhydrous Na$_2$SO$_4$, filtered, and concentrated to give 830 mg of product with a yield of 47%. LCMS (ESI): m/z=255 (M+H)$^+$.

Step 4. N-(1-(1-(1-acetylpiperidin-4-yl)azetidin-3-yl)-3-(difluoromethyl)-1H-pyrazol-4-yl)-6-(1-(1-cyanocyclopropyl)-1H-pyrazol-4-yl)-2-picolinamide

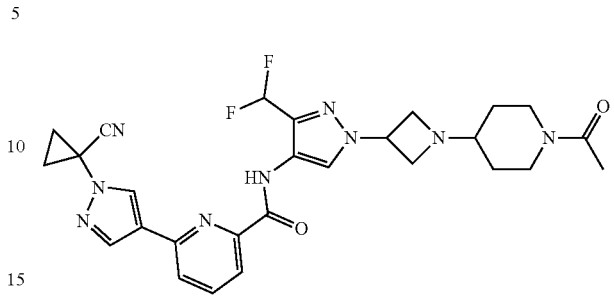

1-(4-(3-(4-Amino-3-(difluoromethyl)-1H-pyrazol-1-yl)azetidin-1-yl)piperidin-1-yl)ethanone (120 mg, 0.38 mmol), 6-(1-(1-cyanocyclopropyl)-1H-pyrazol-4-yl)-2-picolinic acid (97 mg, 0.38 mmol), DIEA (98 mg, 0.76 mmol), HATU (175 mg, 0.46 mmol), and CH$_2$Cl$_2$ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (CH$_2$Cl$_2$:MeOH (v/v)=40:1) to give 175 mg of product with a yield of 84%. LCMS (ESI): m/z=550 (M+H)$^+$. $^1$H NMR (400 MHz, Chloroform-d) δ 10.46 (s, 1H), 8.49 (s, 1H), 8.19 (s, 1H), 8.10-8.05 (m, 2H), 7.91 (t, J=7.7 Hz, 1H), 7.64 (dd, J=7.9, 1.1 Hz, 1H), 6.90 (t, J=54.6 Hz, 1H), 5.01-4.91 (m, 1H), 4.29-4.20 (m, 1H), 3.84 (t, J=7.5 Hz, 2H), 3.80-3.71 (m, 1H), 3.52 (t, J=7.1 Hz, 2H), 3.21-3.11 (m, 1H), 3.04-2.94 (m, 1H), 2.53-2.43 (m, 1H), 2.10 (s, 3H), 1.93-1.87 (m, 4H), 1.80-1.69 (m, 2H), 1.39-1.23 (m, 2H).

Example 10

N-(1-(1-(1-acetylpiperidin-4-yl)azetidin-3-yl)-3-(difluoromethyl)-1H-pyrazol-4-yl)-6-(1-(1-cyanocyclobutyl)-1H-pyrazol-4-yl)-2-picolinamide

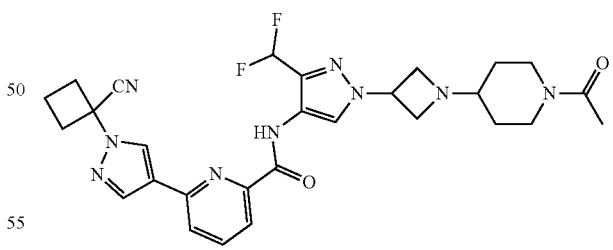

This example was prepared following the method of Example 9. LCMS (ESI): m/z=564 (M+H)$^+$. $^1$H NMR (400 MHz, Chloroform-d) δ 10.50 (s, 1H), 8.49 (s, 1H), 8.26 (s, 1H), 8.16 (s, 1H), 8.06 (dd, J=7.5, 1.0 Hz, 1H), 7.90 (t, J=7.8 Hz, 1H), 7.66 (dd, J=7.9, 1.1 Hz, 1H), 6.88 (t, J=54.6 Hz, 1H), 5.01-4.91 (m, 1H), 4.29-4.20 (m, 1H), 3.84 (t, J=7.5 Hz, 2H), 3.80-3.71 (m, 1H), 3.56-3.49 (m, 2H), 3.20-3.05 (m, 3H), 3.03-2.93 (m, 3H), 2.53-2.43 (m, 1H), 2.43-2.30 (m, 1H), 2.27-2.15 (m, 1H), 2.09 (s, 3H), 1.82-1.64 (m, 2H), 1.31 (m, 2H).

Example 11

N-(1-(1-(1-acetylpiperidin-4-yl)azetidin-3-yl)-3-(difluoromethyl)-1H-pyrazol-4-yl)-6-(1-(1-(aminomethyl)cyclobutyl)-1H-pyrazol-4-yl)-2-picolinamide

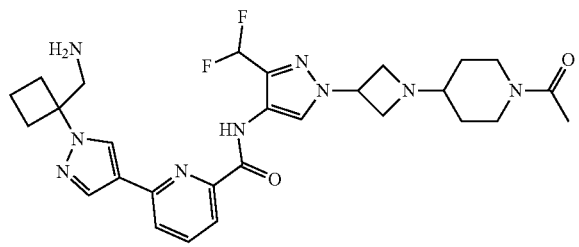 [SMILES: CC(=O)N1CCC(N2CC(n3cc(NC(=O)c4cccc(-c5cnn(C6(CN)CCC6)c5)n4)c(C(F)F)n3)C2)CC1]

N-(1-(1-(1-acetylpiperidin-4-yl)azetidin-3-yl)-3-(difluoromethyl)-1H-pyrazol-4-yl)-6-(1-(1-cyanocyclobutyl)-1H-pyrazol-4-yl)-2-picolinamide (150 mg, 0.27 mmol) was dissolved in MeOH (10 mL) in a 25 mL round-bottom flask and cooled in an ice bath. The above solution was added with anhydrous $COCl_2$ (0.4 mg, 0.003 mmol) and $NaBH_4$ (12 mg, 0.32 mmol) and reacted for 20 min with the temperature being maintained. After the reaction was completed, the solution was diluted with water and extracted with EtOAc. The organic phases were combined, washed with a saturated NaCl solution, dried over anhydrous $Na_2SO_4$, filtered, and concentrated. The residues were purified through silica gel column chromatography ($CH_2Cl_2$:MeOH (v/v)=20:1) to give 120 mg of product with a yield of 79%. LCMS (ESI): m/z=568 (M+H)$^+$. $^1$H NMR (400 MHz, Chloroform-d) δ 10.56 (s, 1H), 8.49 (s, 1H), 8.12 (s, 1H), 8.06 (s, 1H), 8.00 (dd, J=7.6, 0.8 Hz, 1H), 7.86 (t, J=7.8 Hz, 1H), 7.63 (dd, J=7.8, 0.7 Hz, 1H), 6.87 (t, J=54.6 Hz, 1H), 5.01-4.87 (m, 1H), 4.29-4.15 (m, 1H), 3.82 (t, J=7.5 Hz, 2H), 3.78-3.69 (m, 1H), 3.50 (t, J=6.4 Hz, 2H), 3.21 (s, 2H), 3.19-3.11 (m, 1H), 3.02-2.92 (m, 1H), 2.69-2.56 (m, 2H), 2.51-2.31 (m, 3H), 2.09 (s, 3H), 2.07-1.91 (m, 2H), 1.78-1.68 (m, 2H), 1.38-1.20 (m, 2H).

Example 12

N-(1-(1-(1-acetylpiperidin-4-yl)azetidin-3-yl)-3-(difluoromethyl)-1H-pyrazol-4-yl)-6-(1-(2-cyanopropan-2-yl)-1H-pyrazol-4-yl)-2-picolinamide Step 1.
2-(4-Iodo-1H-pyrazol-1-yl)-2-methylpropionitrile

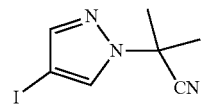

DMSO (50 mL) was added in a 150 mL round-bottom flask and cooled in an ice bath.
Then NaH (3.4 g, 85.6 mmol, 60%) was added and stirred for 20 min. A mixed solution of 2-(4-iodo-1H-pyrazol-1-yl)acetonitrile (5.0 g, 21.4 mmol) and iodomethane (9.1 g, 64.2 mmol) in DMSO (10 mL) was added to the above reaction solution, naturally warmed to room temperature, and reacted for 8 h. After the reaction was completed, the above reaction solution was poured into an icy and saturated $NH_4Cl$ aqueous solution, and the aqueous phase was extracted with EtOAc. The organic phases were combined, washed with a saturated NaCl solution, dried over anhydrous $Na_2SO_4$, filtered, and concentrated. The residues were purified through silica gel column chromatography (PE:EtOAc (v/v)=5:1) to give 4.2 g of product with a yield of 75%. LCMS (ESI): m/z=262 (M+H)$^+$.

Step 2. 6-(1-(2-Cyanopropan-2-yl)-1H-pyrazol-4-yl)-2-picolinic Acid

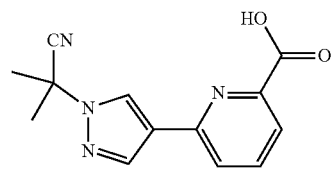 [SMILES: CC(C)(C#N)n1cc(-c2cccc(C(=O)O)n2)cn1]

Under the protection of nitrogen, 2-(4-iodo-1H-pyrazol-1-yl)-2-methylpropionitrile (2.0 g, 7.7 mmol), bis(pinacolato)diboron (3.9 g, 15.4 mmol), Pd(dppf)$Cl_2$ (0.5 g, 0.7 mmol), AcOK (2.3 g, 23.1 mmol), and DMF (30 mL) were added in a 100 mL round-bottom flask, heated to 100° C., and reacted for 2 h. After the reaction was completed, the solution was filtered and the filter residues were washed with EtOAc. The filtrate was added with $H_2O$ and extracted with EtOAc. The organic phases were combined, washed with a saturated NaCl solution, dried over anhydrous $Na_2SO_4$, filtered, and concentrated. The obtained residues were directly used in the next step.

Under the protection of nitrogen, the residues obtained above, 6-bromo-2-picolinic acid (1.5 g, 7.7 mmol), Pd(PPh$_3$)$_4$ (0.8 g, 0.7 mmol), $Na_2CO_3$ (2.4 g, 23.1 mmol), dioxane (40 mL), and $H_2O$ (10 mL) were added in a 100 mL round-bottom flask, heated to 80° C., and reacted for 10 h. After the reaction was completed, the solution was filtered and the filter residues were washed with EtOAc. The filtrate was added with $H_2O$ and extracted with EtOAc. The aqueous phase was adjusted with 1 M HCl to a pH of 1, extracted with EtOAc, washed with a saturated NaCl solution, dried over anhydrous $Na_2SO_4$, filtered, and concentrated to give 1.6 g of product with a yield of 81%. LCMS (ESI): m/z=257 (M+H)$^+$.

Step 3. N-(1-(1-(1-acetylpiperidin-4-yl)azetidin-3-yl)-3-(difluoromethyl)-1H-pyrazol-4-yl)-6-(1-(2-cyanopropan-2-yl)-1H-pyrazol-4-yl)-2-picolinamide

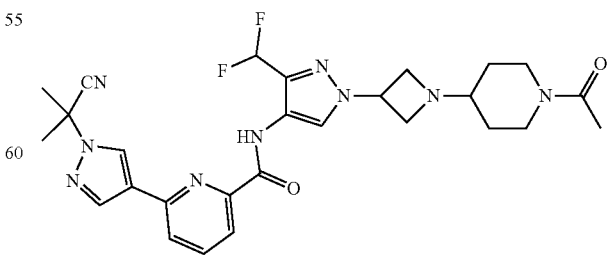

1-(4-(3-(4-Amino-3-(difluoromethyl)-1H-pyrazol-1-yl)azetidin-1-yl)piperidin-1-yl)ethanone (120 mg, 0.38 mmol), 6-(1-(2-cyanopropan-2-yl)-1H-pyrazol-4-yl)-2-picolinic acid (97 mg, 0.38 mmol), DIEA (98 mg, 0.76 mmol), HATU (175 mg, 0.46 mmol), and CH$_2$Cl$_2$ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (CH$_2$Cl$_2$:MeOH (v/v)=40:1) to give 132 mg of product with a yield of 63%. LCMS (ESI): m/z=552 (M+H)$^+$. $^1$H NMR (400 MHz, Chloroform-d) δ 10.52 (s, 1H), 8.49 (s, 1H), 8.29 (s, 1H), 8.13 (s, 1H), 8.05 (dd, J=7.5, 1.1 Hz, 1H), 7.90 (t, J=7.8 Hz, 1H), 7.66 (dd, J=7.9, 1.1 Hz, 1H), 6.88 (t, J=54.6 Hz, 1H), 5.00-4.90 (m, 1H), 4.28-4.19 (m, 1H), 3.83 (t, J=7.5 Hz, 2H), 3.79-3.70 (m, 1H), 3.55-3.48 (m, 2H), 3.21-3.11 (m, 1H), 3.04-2.94 (m, 1H), 2.51-2.42 (m, 1H), 2.09 (s, 3H), 2.08 (s, 6H), 1.81-1.67 (m, 2H), 1.41-1.22 (m, 2H).

Example 13

N-(1-(1-(1-acetylpiperidin-4-yl)azetidin-3-yl)-3-(difluoromethyl)-1H-pyrazol-4-yl)-6-(1-(1-amino-2-methylpropan-2-yl)-1H-pyrazol-4-yl)-2-picolinamide

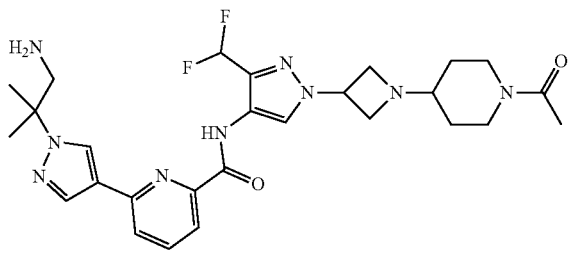 [SMILES: CC(=O)N1CCC(N2CC(n3cc(NC(=O)c4cccc(-c5cnn(C(C)(C)CN)c5)n4)c(C(F)F)n3)C2)CC1]

This example was obtained by reducing Example 12 with reference to the steps in Example 11. LCMS (ESI): m/z=556 (M+H)$^+$. $^1$H NMR (400 MHz, Chloroform-d) δ 10.57 (s, 1H), 8.49 (s, 1H), 8.20 (s, 1H), 8.06 (s, 1H), 7.99 (d, J=7.4 Hz, 1H), 7.86 (t, J=7.8 Hz, 1H), 7.63 (d, J=7.9 Hz, 1H), 6.88 (t, J=54.6 Hz, 1H), 4.99-4.90 (m, 1H), 4.28-4.19 (m, 1H), 3.83 (t, J=7.6 Hz, 2H), 3.78-3.70 (m, 1H), 3.55-3.47 (m, 2H), 3.20-3.11 (m, 1H), 3.08 (s, 2H), 3.03-2.93 (m, 1H), 2.51-2.42 (m, 1H), 2.09 (s, 3H), 1.81-1.68 (m, 2H), 1.63 (s, 6H), 1.39-1.21 (m, 2H).

Example 14

N-(1-(1-(1-acetylpiperidin-4-yl)azetidin-3-yl)-3-(difluoromethyl)-1H-pyrazol-4-yl)-6-(1-(1-(hydroxymethyl)cyclobutyl)-1H-pyrazol-4-yl)-2-picolinamide Step 1. Ethyl 2-(4-iodo-1H-pyrazol-1-yl)acetate

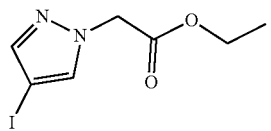

In a 250 mL round-bottom flask, 4-iodopyrazole (10.0 g, 51.5 mmol) was dissolved in DMF (100 mL), added with ethyl bromoacetate (9.4 g, 56.6 mmol), and K$_2$CO$_3$ (14.0 g, 103.0 mmol), and then heated to 50° C. and reacted for 3 h. After the reaction was completed, the solution was diluted with water and layers were separated. The aqueous phase was extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=5:1) to give 11.6 g of product with a yield of 80%. LCMS (ESI): m/z=281 (M+H)$^+$.

Step 2. Ethyl 1-(4-iodo-1H-pyrazol-1-yl)cyclobutane-1-carboxylate

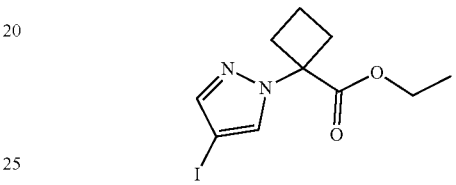

DMSO (50 mL) was added in a 150 mL round-bottom flask and cooled in an ice bath. Then NaH (2.8 g, 71.4 mmol, 60%) was added and stirred for 20 min. A mixed solution of ethyl 2-(4-iodo-1H-pyrazol-1-yl)acetate (5.0 g, 17.8 mmol) and 1,3-dibromopropane (10.8 g, 53.4 mmol) in DMSO (10 mL) was added to the above reaction solution, naturally warmed to room temperature, and reacted for 8 h. After the reaction was completed, the above reaction solution was poured into an icy and saturated NH$_4$Cl aqueous solution, and the aqueous phase was extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=5:1) to give 3.6 g of product with a yield of 63%. LCMS (ESI): m/z=321 (M+H)$^+$.

Step 3. (1-(4-Iodo-1H-pyrazol-1-yl)cyclobutyl)methanol

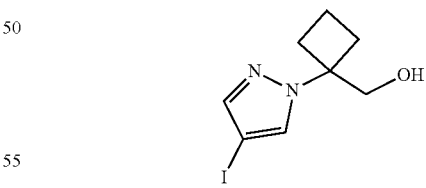

Under the protection of nitrogen, in a 250 mL three-necked round-bottom flask equipped with a thermometer, ethyl 1-(1-(t-butylcarbonyl)azetidin-3-yl)-4-nitro-1H-pyrazole-3-carboxylate (3.6 g, 11.2 mmol) was dissolved in CH$_2$Cl$_2$ (50 mL) and cooled in an ice salt bath. The internal temperature was kept below −10° C., a solution of 1 M DIBAL-H in n-hexane (33 mL) was slowly added dropwise into the above solution, and then the above reaction solution was poured into a saturated NH$_4$Cl solution (100 mL), stirred, and filtered. The filtrate was extracted with EtOAc.

The organic phases were combined, washed with a saturated NaCl solution, dried over anhydrous Na$_2$SO$_4$, filtered, and concentrated. The residues were purified through silica gel column chromatography (PE:EtOAc (v/v)=3:1) to give 1.7 g of product with a yield of 54%. LCMS (ESI): m/z=279 (M+H)$^+$.

Step 4. Methyl 6-(1-(1-(hydroxymethyl)cyclobutane)-1H-pyrazol-4-yl)-2-picolinate

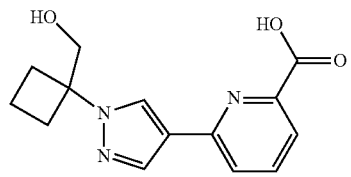 [SMILES: O=C(O)c1cccc(-c2cnn(C3(CO)CCC3)c2)n1]

Under the protection of nitrogen, (1-(4-iodo-1H-pyrazol-1-yl)cyclobutyl)methanol (1.7 g, 6.1 mmol), bis(pinacolato)diboron (3.1 g, 12.2 mmol), Pd(dppf)Cl$_2$ (439 mg, 0.6 mmol), AcOK (1.8 g, 18.3 mmol), and DMF (20 mL) were added in a 100 mL round-bottom flask, heated to 100° C., and reacted for 2 h. After the reaction was completed, the solution was filtered and the filter residues were washed with EtOAc. The filtrate was added with H$_2$O and extracted with EtOAc. The organic phases were combined, washed with a saturated NaCl solution, dried over anhydrous Na$_2$SO$_4$, filtered, and concentrated. The obtained residues were directly used in the next step.

Under the protection of nitrogen, the residues obtained above, methyl 6-bromo-2-picolinate (1.3 g, 6.1 mmol), Pd(PPhs)$_4$ (693 mg, 0.6 mmol), Na$_2$CO$_3$ (1.3 g, 12.2 mmol), dioxane (20 mL), and H$_2$O (5 mL) were added in a 100 mL round-bottom flask, heated to 80° C., and reacted for 2 h. After the reaction was completed, the solution was filtered and the filter residues were washed with EtOAc. The filtrate was added with H$_2$O and extracted with EtOAc. The organic phases were combined, washed with a saturated NaCl solution, dried over anhydrous Na$_2$SO$_4$, filtered, and concentrated. The residues were purified through silica gel column chromatography (PE:EtOAc (v/v)=2:1) to give 1.2 g of product with a yield of 68%. LCMS (ESI): m/z=288 (M+H)$^+$.

Step 5. 6-(1-(1-(Hydroxymethyl)cyclobutane)-1H-pyrazol-4-yl)-2-picolinic Acid

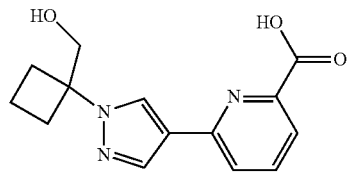 [SMILES: O=C(O)c1cccc(-c2cnn(C3(CO)CCC3)c2)n1]

Methyl 6-(1-(1-(hydroxymethyl)cyclobutane)-1H-pyrazol-4-yl)-2-picolinate (1.2 g, 4.2 mmol) was dissolved in MeOH (20 mL), added with a solution of NaOH (1 M 20 mL), and reacted at room temperature for 1 h. After the reaction was completed, the solution was concentrated to remove MeOH, diluted with water, and extracted with EtOAc. The aqueous phase was adjusted with 4 M hydrochloric acid to a pH of 3. The solids were precipitated, filtered, and washed with H$_2$O to give 1.0 g of solids with a yield of 87%. LCMS (ESI): m/z=274 (M+H)$^+$.

Step 6. N-(1-(1-(1-acetylpiperidin-4-yl)azetidin-3-yl)-3-(difluoromethyl)-1H-pyrazol-4-yl)-6-(1-(1-(hydroxymethyl)cyclobutyl)-1H-pyrazol-4-yl)-2-picolinamide

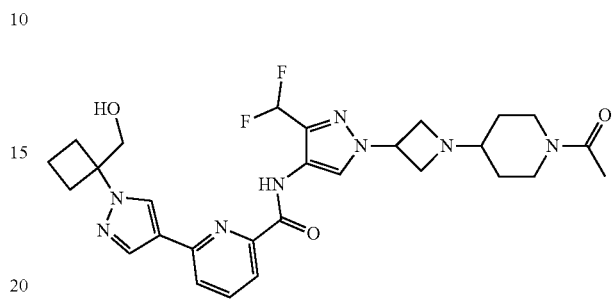

1-(4-(3-(4-Amino-3-(difluoromethyl)-1H-pyrazol-1-yl)azetidin-1-yl)piperidin-1-yl)ethanone (120 mg, 0.38 mmol), 6-(1-(1-(hydroxymethyl)cyclobutane)-1H-pyrazol-4-yl)-2-picolinic acid (104 mg, 0.38 mmol), DIEA (98 mg, 0.76 mmol), HATU (175 mg, 0.46 mmol), and CH$_2$Cl$_2$ (5 mL) were added in a 25 mL round-bottom flask and stirred at room temperature for 1 h. After the reaction was completed, the solution was diluted with water and extracted with CH$_2$Cl$_2$. The organic phases were combined, washed with a saturated NaCl solution, dried over anhydrous Na$_2$SO$_4$, filtered, and concentrated. The residues were purified through silica gel column chromatography (CH$_2$Cl$_2$:MeOH (v/v)=20:1) to give 110 mg of product with a yield of 51%. LCMS (ESI): m/z=569 (M+H)$^+$. $^1$H NMR (400 MHz, Chloroform-d) δ 10.51 (s, 1H), 8.51 (s, 1H), 8.09 (s, 1H), 8.07-8.00 (m, 2H), 7.92-7.84 (m, 1H), 7.67-7.61 (m, 1H), 6.89 (t, J=54.6 Hz, 1H), 5.20-5.06 (m, 1H), 5.03-4.91 (m, 1H), 4.43-4.16 (m, 2H), 4.04 (s, 2H), 3.90-3.81 (m, 2H), 3.80-3.69 (m, 1H), 3.61-3.44 (m, 2H), 3.26-3.10 (m, 1H), 3.04-2.91 (m, 1H), 2.85-2.41 (m, 4H), 2.11 (s, 3H), 2.06-1.95 (m, 1H), 1.83-1.67 (m, 2H), 1.39-1.30 (m, 2H).

Example 15

N-(1-(1-(1-acetylpiperidin-4-yl)azetidin-3-yl)-3-(difluoromethyl)-1H-pyrazol-4-yl)-6-(1-(2-hydroxy-2-methylpropyl)-1H-pyrazol-4-yl)-2-picolinamide Step 1. 1-(4-Iodo-1H-pyrazol-1-yl)-2-methylpropan-2-ol

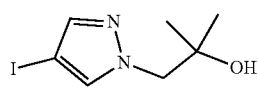

In a 150 mL round-bottom flask, 4-iodopyrazole (5.0 g, 25.7 mmol) was dissolved in DMF (50 mL), added with 1-chloro-2-methyl-2-propanol (3.1 g, 28.3 mmol), and K$_3$PO$_4$ (10.9 g, 51.4 mmol), and then heated to 50° C. and reacted for 10 h. After the reaction was completed, the solution was diluted with water and layers were separated. The aqueous phase was extracted with EtOAc. The organic phases were combined, washed with a saturated NaCl solution, dried over anhydrous Na₂SO₄, filtered, and concentrated. The residues were purified through silica gel column chromatography (PE:EtOAc (v/v)=3:1) to give 4.2 g of product with a yield of 58%. LCMS (ESI): m/z=281 (M+H)⁺.

Step 2. Methyl 6-(1-(2-hydroxy-2-methylpropyl)-1H-pyrazol-4-yl)-2-picolinate

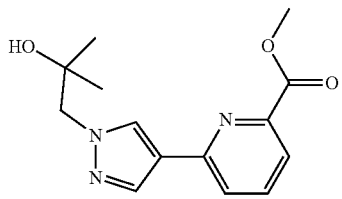 [SMILES: COC(=O)c1cccc(-c2cnn(CC(C)(C)O)c2)n1]

Under the protection of nitrogen, 1-(4-iodo-1H-pyrazol-1-yl)-2-methylpropan-2-ol (4.2 g, 15.0 mmol), bis(pinacolato)diboron (7.6 g, 30.0 mmol), Pd(dppf)Cl₂ (1.1 g, 1.5 mmol), AcOK (4.4 g, 45 mmol), and DMF (50 mL) were added in a 100 mL round-bottom flask, heated to 100° C., and reacted for 2 h. After the reaction was completed, the solution was filtered and the filter residues were washed with EtOAc. The filtrate was added with H₂O and extracted with EtOAc. The organic phases were combined, washed with a saturated NaCl solution, dried over anhydrous Na₂SO₄, filtered, and concentrated. The obtained residues were directly used in the next step.

Under the protection of nitrogen, the residues obtained above, methyl 6-bromo-2-picolinate (3.2 g, 15.0 mmol), Pd(PPh₃)₄ (1.7 g, 1.5 mmol), Na₂CO₃ (3.2 g, 30.0 mmol), dioxane (50 mL), and H₂O (10 mL) were added in a 100 mL round-bottom flask, heated to 80° C., and reacted for 2 h. After the reaction was completed, the solution was filtered and the filter residues were washed with EtOAc. The filtrate was added with H₂O and extracted with EtOAc. The organic phases were combined, washed with a saturated NaCl solution, dried over anhydrous Na₂SO₄, filtered, and concentrated. The residues were purified through silica gel column chromatography (PE:EtOAc (v/v)=3:1) to give 3.0 g of product with a yield of 73%. LCMS (ESI): m/z=276 (M+H)⁺.

Step 3. 6-(1-(2-Hydroxy-2-methylpropyl)-1H-pyrazol-4-yl)-2-picolinic Acid

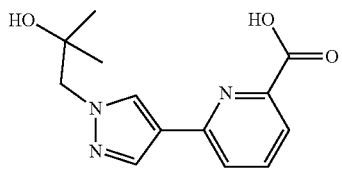 [SMILES: CC(C)(O)Cn1cc(-c2cccc(C(=O)O)n2)cn1]

Methyl 6-(1-(2-hydroxy-2-methylpropyl)-1H-pyrazol-4-yl)-2-picolinate (3.0 g, 10.9 mmol) was dissolved in MeOH (30 mL), added with a solution of NaOH (1 M 30 mL), and reacted at room temperature for 1 h. After the reaction was completed, the solution was concentrated to remove MeOH, diluted with water, and extracted with EtOAc. The aqueous phase was adjusted with 4 M hydrochloric acid to a pH of 3. The solids were precipitated, filtered, and washed with H₂O to give 2.5 g of solids with a yield of 88%. LCMS (ESI): m/z=262 (M+H)⁺.

Step 4. N-(1-(1-(1-acetylpiperidin-4-yl)azetidin-3-yl)-3-(difluoromethyl)-1H-pyrazol-4-yl)-6-(1-(2-hydroxy-2-methylpropyl)-1H-pyrazol-4-yl)-2-picolinamide

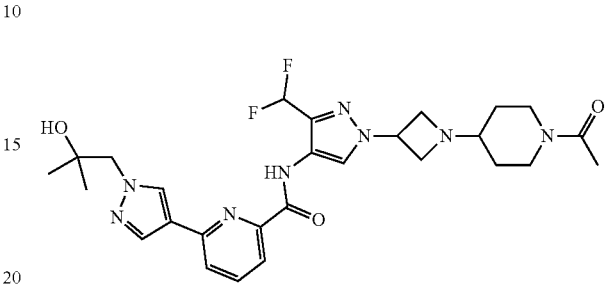

1-(4-(3-(4-Amino-3-(difluoromethyl)-1H-pyrazol-1-yl)azetidin-1-yl)piperidin-1-yl)ethanone (120 mg, 0.38 mmol), 6-(1-(2-hydroxy-2-methylpropyl)-1H-pyrazol-4-yl)-2-picolinic acid (99 mg, 0.38 mmol), DIEA (98 mg, 0.76 mmol), HATU (175 mg, 0.46 mmol), and CH₂Cl₂ (5 mL) were added in a 25 mL round-bottom flask and stirred at room temperature for 1 h. After the reaction was completed, the solution was diluted with water and extracted with CH₂Cl₂. The organic phases were combined, washed with a saturated NaCl solution, dried over anhydrous Na₂SO₄, filtered, and concentrated. The residues were purified through silica gel column chromatography (CH₂Cl₂:MeOH (v/v)=20:1) to give 160 mg of product with a yield of 76%. LCMS (ESI): m/z=557 (M+H)⁺. ¹H NMR (400 MHz, Chloroform-d) δ 10.49 (s, 1H), 8.50 (s, 1H), 8.08 (s, 1H), 8.05-8.00 (m, 2H), 7.88 (t, J=7.8 Hz, 1H), 7.64 (dd, J=8.1, 1.1 Hz, 1H), 6.88 (t, J=54.7 Hz, 1H), 5.00-4.90 (m, 1H), 4.28-4.19 (m, 1H), 4.16 (s, 2H), 3.83 (t, J=7.5 Hz, 2H), 3.75 (d, J=13.6 Hz, 1H), 3.62 (s, 1H), 3.55-3.47 (m, 2H), 3.21-3.11 (m, 1H), 3.03-2.94 (m, 1H), 2.52-2.42 (m, 1H), 2.09 (s, 3H), 1.80-1.72 (m, 2H), 1.41-1.26 (m, 2H), 1.24 (s, 6H).

Example 16

N-(1-(1-(1-acetylpiperidin-4-yl)azetidin-3-yl)-3-(difluoromethyl)-1H-pyrazol-4-yl)-6-(1-(1-hydroxy-2-methylpropyl-2-yl)-1H-pyrazol-4-yl)-2-picolinamide

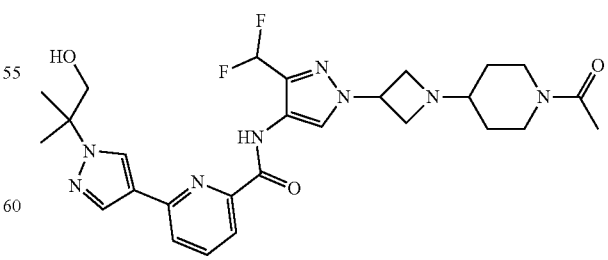

This example was prepared with reference to the steps in Example 14. LCMS (ESI): m/z=557 (M+H)⁺. ¹H NMR (400 MHz, DMSO-d₆) δ 10.43 (s, 1H), 8.51 (s, 1H), 8.49 (s, 1H), 8.16 (s, 1H), 8.06-7.94 (m, 2H), 7.89 (dd, J=7.2, 1.3 Hz, 1H), 7.27 (t, J=54.2 Hz, 1H), 5.14-5.04 (m, 1H), 5.00 (t, J=5.7 Hz, 1H), 4.04-3.94 (m, 1H), 3.75-3.64 (m, 3H), 3.62 (d, J=5.6 Hz, 2H), 3.45-3.36 (m, 2H), 3.17-3.06 (m, 1H), 2.95-2.84 (m, 1H), 2.45-2.36 (m, 1H), 1.98 (s, 3H), 1.74-1.59 (m, 2H), 1.54 (s, 6H), 1.26-1.12 (m, 1H), 1.11-1.00 (m, 1H).

Example 17

6-(1-(1-Amino-2-methylpropan-2-yl)-1H-pyrazol-4-yl)-N-(3-(difluoromethyl)-1-(1-(1-(dimethylcarbamoyl)piperidin-4-yl)azetidin-3-yl)-1H-pyrazol-4-yl)-2-picolinamide

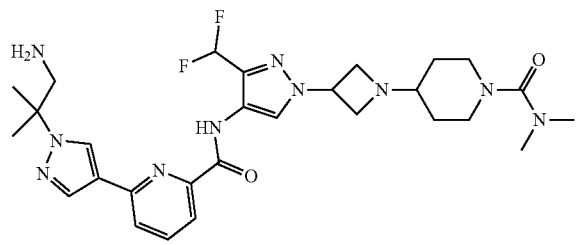 [SMILES: COC(=O)N1CCC(N2CC(n3cc(NC(=O)c4cccc(-c5cnn(C(C)(C)CN)c5)n4)c(C(F)F)n3)C2)CC1]

This example was prepared following the method of Example 13. LCMS (ESI): m/z=585 (M+H)+. 1H NMR (400 MHz, Chloroform-d) δ 10.58 (s, 1H), 8.50 (s, 1H), 8.21 (s, 1H), 8.07 (s, 1H), 8.00 (d, J=7.7 Hz, 1H), 7.86 (t, J=7.7 Hz, 1H), 7.64 (d, J=8.0 Hz, 1H), 6.89 (t, J=54.6 Hz, 1H), 5.00-4.91 (m, 1H), 3.83 (t, J=7.7 Hz, 2H), 3.64-3.56 (m, 2H), 3.51 (t, J=7.6 Hz, 2H), 3.09 (s, 2H), 2.90-2.79 (m, 8H), 2.42-2.33 (m, 1H), 1.79-1.71 (m, 2H), 1.65 (s, 6H), 1.39-1.24 (m, 2H).

Example 18

Methyl 4-(3-(4-(6-(1-(1-amino-2-methylpropan-2-yl)-1H-pyrazol-4-yl)-2-picolinamide)-3-(difluoromethyl)-1H-pyrazol-1-yl)azetidin-1-yl)piperidine-1-carboxylate

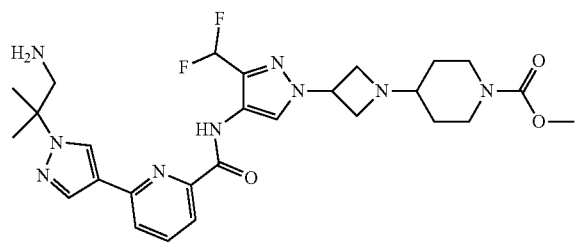

This example was prepared following the method of Example 13. LCMS (ESI): m/z=572 (M+H)+. 1H NMR (400 MHz, Chloroform-d) δ 10.58 (s, 1H), 8.50 (s, 1H), 8.21 (s, 1H), 8.07 (s, 1H), 8.00 (d, J=7.5 Hz, 1H), 7.86 (t, J=7.8 Hz, 1H), 7.64 (d, J=7.8 Hz, 1H), 6.88 (t, J=54.6 Hz, 1H), 5.00-4.91 (m, 1H), 4.05-3.89 (m, 2H), 3.87-3.79 (m, 2H), 3.70 (s, 3H), 3.53-3.46 (m, 2H), 3.09 (s, 2H), 3.04-2.95 (m, 2H), 2.44-2.35 (m, 1H), 1.76-1.67 (m, 2H), 1.65 (s, 6H), 1.35-1.21 (m, 2H).

Example 19

N-(1-(1-(1-acetylpiperidin-4-yl)azetidin-3-yl)-3-(difluoromethyl)-1H-pyrazol-4-yl)-6-(1H-pyrazol-4-yl)-2-picolinamide

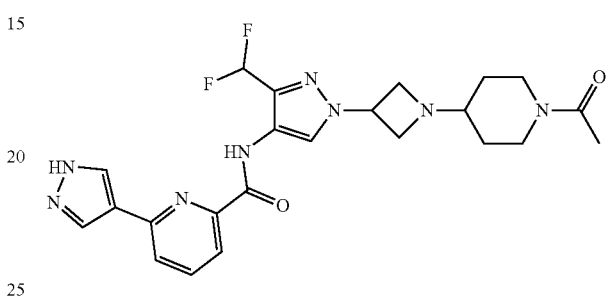

This example was prepared following the method of Example 5. LCMS (ESI): m/z=485 (M+H)+. 1H NMR (400 MHz, Chloroform-d) δ 10.52 (s, 1H), 8.51 (s, 1H), 8.19 (s, 2H), 8.05 (d, J=7.7 Hz, 1H), 7.89 (t, J=7.8 Hz, 1H), 7.69 (d, J=7.9 Hz, 1H), 6.89 (t, J=54.6 Hz, 1H), 5.01-4.91 (m, 1H), 4.29-4.21 (m, 1H), 3.84 (t, J=7.6 Hz, 2H), 3.80-3.71 (m, 1H), 3.52 (t, J=7.3 Hz, 2H), 3.21-3.12 (m, 1H), 3.04-2.94 (m, 1H), 2.52-2.43 (m, 1H), 2.11 (s, 3H), 1.82-1.68 (m, 2H), 1.39-1.23 (m, 2H).

Example 20

N-(3-(difluoromethyl)-1-(1-(1-(dimethylcarbamoyl)piperidin-4-yl)azetidin-3-yl)-1H-pyrazol-4-yl)-6-(1H-pyrazol-4-yl)-2-picolinamide

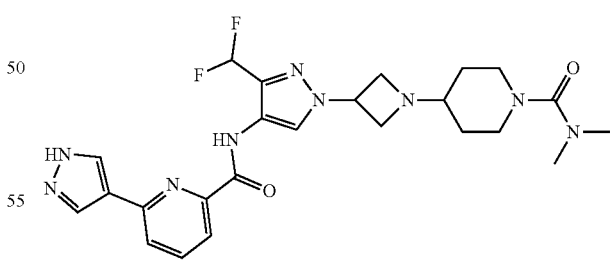

This example was prepared following the method of Example 5. LCMS (ESI): m/z=514 (M+H)+. 1H NMR (400 MHz, Chloroform-d) δ 10.51 (s, 1H), 8.51 (s, 1H), 8.18 (s, 2H), 8.04 (d, J=7.8 Hz, 1H), 7.89 (t, J=7.8 Hz, 1H), 7.68 (d, J=8.0 Hz, 1H), 6.90 (t, J=54.6 Hz, 1H), 5.01-4.92 (m, 1H), 3.84 (t, J=7.8 Hz, 2H), 3.65-3.58 (m, 2H), 3.52 (t, J=7.6 Hz, 2H), 2.90-2.79 (m, 8H), 2.44-2.34 (m, 1H), 1.80-1.71 (m, 2H), 1.40-1.25 (m, 2H).

Example 21

Methyl 4-(3-(4-(6-(1H-pyrazol-4-yl)-2-picolinamide)-3-(difluoromethyl)-1H-pyrazol-1-yl)azetidin-1-yl)piperidine-1-carboxylate

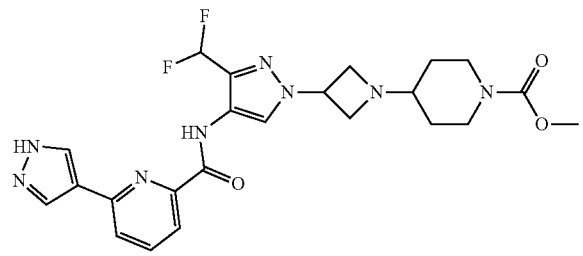 [SMILES: COC(=O)N1CCC(N2CC(n3cc(NC(=O)c4cccc(-c5cn[nH]c5)n4)c(C(F)F)n3)C2)CC1]

This example was prepared following the method of Example 5. LCMS (ESI): m/z=501 (M+H)+. 1H NMR (400 MHz, Chloroform-d) δ 10.51 (s, 1H), 8.51 (s, 1H), 8.19 (s, 2H), 8.05 (d, J=7.5 Hz, 1H), 7.89 (t, J=7.7 Hz, 1H), 7.69 (d, J=7.9 Hz, 1H), 6.89 (t, J=54.7 Hz, 1H), 5.01-4.91 (m, 1H), 4.07-3.91 (m, 2H), 3.84 (t, J=7.6 Hz, 2H), 3.70 (s, 3H), 3.51 (d, J=7.6 Hz, 2H), 3.04-2.94 (m, 2H), 2.47-2.36 (m, 1H), 1.79-1.67 (m, 2H), 1.35-1.21 (m, 2H).

Example 22

N-(1-(1-(1-acryloylpiperidin-4-yl)azetidin-3-yl)-3-(difluoromethyl)-1H-pyrazol-4-yl)-6-(1H-pyrazol-4-yl)-2-picolinamide

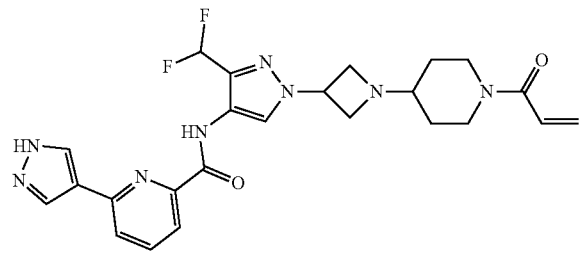 [SMILES: C=CC(=O)N1CCC(N2CC(n3cc(NC(=O)c4cccc(-c5cc[nH]n5)n4)c(C(F)F)n3)C2)CC1]

This example was prepared following the method of Example 5. LCMS (ESI): m/z=497 (M+H)+. 1H NMR (400 MHz, Chloroform-d) δ 10.51 (s, 1H), 8.51 (s, 1H), 8.18 (s, 2H), 8.04 (d, J=7.6 Hz, 1H), 7.89 (t, J=7.7 Hz, 1H), 7.68 (d, J=7.7 Hz, 1H), 6.89 (t, J=54.5 Hz, 1H), 6.59 (dd, J=16.8, 10.6 Hz, 1H), 6.27 (dd, J=16.8, 1.9 Hz, 1H), 5.69 (dd, J=10.7, 1.9 Hz, 1H), 5.01-4.91 (m, 1H), 4.34-4.21 (m, 1H), 3.96-3.77 (m, 3H), 3.58-3.49 (m, 2H), 3.29-2.94 (m, 2H), 2.56-2.43 (m, 1H), 1.83-1.68 (m, 2H), 1.44-1.22 (m, 2H).

Example 23

N-(1-(1-(1-acryloylpiperidin-4-yl)azetidin-3-yl)-3-(difluoromethyl)-1H-pyrazol-4-yl)-6-(1H-pyrazol-3-yl)-2-picolinamide

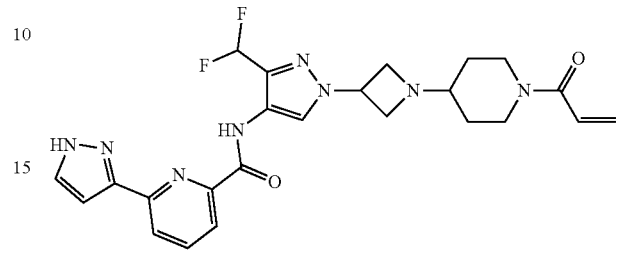

This example was prepared following the method of Example 5. LCMS (ESI): m/z=497 (M+H)+. 1H NMR (400 MHz, Chloroform-d) δ 10.45 (s, 1H), 8.51 (s, 1H), 8.16 (d, J=7.8 Hz, 1H), 8.11 (d, J=7.8 Hz, 1H), 7.97 (t, J=7.8 Hz, 1H), 7.71 (d, J=2.2 Hz, 1H), 7.03-7.01 (m, 1H), 6.90 (t, J=54.7 Hz, 1H), 6.59 (dd, J=16.9, 10.6 Hz, 1H), 6.27 (dd, J=16.8, 2.0 Hz, 1H), 5.68 (dd, J=10.6, 1.9 Hz, 1H), 5.04-4.90 (m, 1H), 4.35-4.20 (m, 1H), 3.96-3.77 (m, 3H), 3.54 (t, J=7.3 Hz, 2H), 3.30-3.02 (m, 2H), 2.58-2.44 (m, 1H), 1.85-1.70 (m, 2H), 1.43-1.29 (m, 2H).

Example 24

N-(1-(1-(1-acetylpiperidin-4-yl)azetidin-3-yl)-3-(difluoromethyl)-1H-pyrazol-4-yl)-6-(1H-pyrazole-3-yl)-2-picolinamide

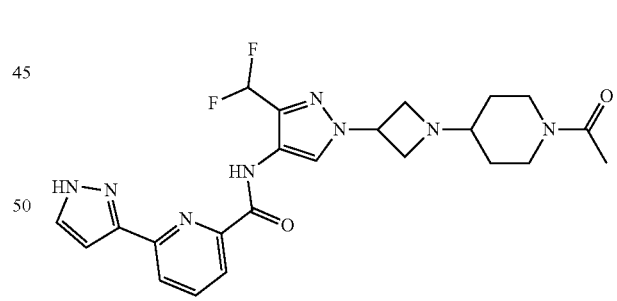

This example was prepared following the method of Example 5. LCMS (ESI): m/z=485 (M+H)+. 1H NMR (400 MHz, Chloroform-d) δ 10.45 (s, 1H), 8.51 (s, 1H), 8.16 (d, J=7.7 Hz, 1H), 8.11 (d, J=7.9 Hz, 1H), 7.97 (t, J=7.8 Hz, 1H), 7.71 (d, J=2.3 Hz, 1H), 7.05-7.00 (m, 1H), 6.83 (d, J=54.6 Hz, 1H), 5.03-4.90 (m, 1H), 4.35-4.19 (m, 1H), 3.85 (t, J=7.4 Hz, 2H), 3.80-3.71 (m, 1H), 3.53 (t, J=7.2 Hz, 2H), 3.24-3.10 (m, 1H), 3.06-2.93 (m, 1H), 2.56-2.41 (m, 1H), 2.11 (s, 3H), 1.83-1.69 (m, 2H), 1.40-1.29 (m, 2H).

Example 25

Methyl 4-(3-(4-(6-(1H-pyrazol-3-yl)-2-picolinamide)-3-(difluoromethyl)-1H-pyrazol-1-yl)azetidin-1-yl)piperidine-1-carboxylate

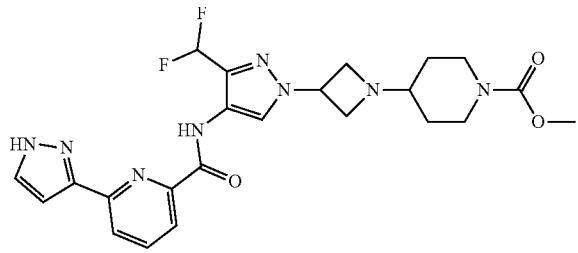 [SMILES: COC(=O)N1CCC(N2CC(n3cc(NC(=O)c4cccc(-c5cc[nH]n5)n4)c(C(F)F)n3)C2)CC1]

This example was prepared following the method of Example 5. LCMS (ESI): m/z=501 (M+H)+. 1H NMR (400 MHz, Chloroform-d) δ 10.50 (s, 1H), 8.55 (s, 1H), 8.21 (d, J=7.8 Hz, 1H), 8.16 (d, J=7.9 Hz, 1H), 8.01 (t, J=7.8 Hz, 1H), 7.76 (d, J=2.3 Hz, 1H), 7.07 (d, J=2.3 Hz, 1H), 6.88 (t, J=54.8 Hz, 1H), 5.12-4.96 (m, 1H), 4.17-3.99 (m, 2H), 3.94 (t, J=7.5 Hz, 2H), 3.76 (s, 3H), 3.60 (t, J=7.5 Hz, 2H), 3.12-2.97 (m, 2H), 2.57-2.42 (m, 1H), 1.87-1.71 (m, 2H), 1.43-1.32 (m, 2H).

Example 26

N-(3-(difluoromethyl)-1-(1-(1-propionylpiperidin-4-yl)azetidin-3-yl)-1H-pyrazol-4-yl)-6-(1H-pyrazol-3-yl)-2-picolinamide

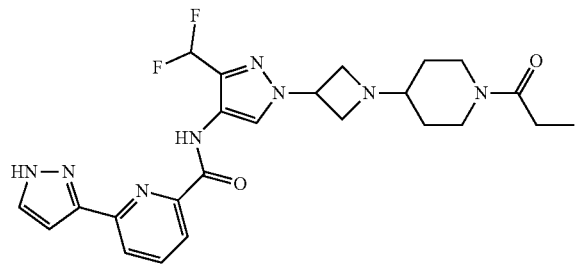 [SMILES: CCC(=O)N1CCC(N2CC(n3cc(NC(=O)c4cccc(-c5cc[nH]n5)n4)c(C(F)F)n3)C2)CC1]

This example was prepared following the method of Example 5. LCMS (ESI): m/z=499 (M+H)+. 1H NMR (400 MHz, Chloroform-d) δ 10.45 (s, 1H), 8.50 (s, 1H), 8.16 (d, J=7.5 Hz, 1H), 8.11 (d, J=8.0 Hz, 1H), 7.96 (t, J=7.8 Hz, 1H), 7.71 (d, J=2.3 Hz, 1H), 7.02 (d, J=2.3 Hz, 1H), 6.90 (t, J=54.6 Hz, 1H), 5.10-4.91 (m, 1H), 4.42-4.25 (m, 1H), 4.02-3.87 (m, 2H), 3.87-3.76 (m, 1H), 3.68-3.50 (m, 2H), 3.19-2.89 (m, 2H), 2.65-2.45 (m, 1H), 2.36 (q, J=7.5 Hz, 2H), 1.84-1.71 (m, 2H), 1.42-1.30 (m, 2H), 1.16 (t, J=7.4 Hz, 3H).

Example 27

N-(3-(difluoromethyl)-1-(1-(1-(2-hydroxyacetyl)piperidin-4-yl)azetidin-3-yl)-1H-pyrazol-4-yl)-6-(1H-pyrazol-3-yl)-2-picolinamide

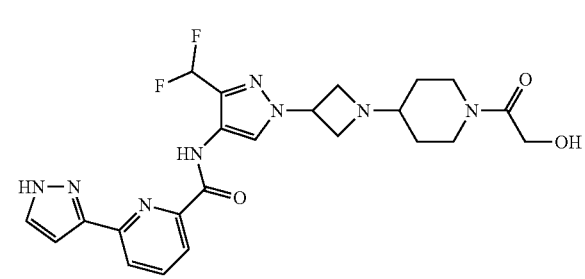 [SMILES: O=C(Nc1cn(C2CN(C3CCN(C(=O)CO)CC3)C2)nc1C(F)F)c1cccc(-c2cc[nH]n2)n1]

This example was prepared following the method of Example 5. LCMS (ESI): m/z=501 (M+H)+. 1H NMR (400 MHz, Chloroform-d) δ 10.45 (s, 1H), 8.51 (s, 1H), 8.16 (d, J=7.6 Hz, 1H), 8.11 (d, J=8.0 Hz, 1H), 7.97 (t, J=7.8 Hz, 1H), 7.71 (d, J=2.3 Hz, 1H), 7.02 (d, J=2.3 Hz, 1H), 6.90 (t, J=54.6 Hz, 1H), 5.08-4.91 (m, 1H), 4.27-4.09 (m, 3H), 3.98-3.79 (m, 2H), 3.66-3.44 (m, 3H), 3.27-2.94 (m, 2H), 2.67-2.47 (m, 1H), 1.87-1.68 (m, 2H), 1.48-1.33 (m, 2H).

Example 28

N-(3-(difluoromethyl)-1-(1-(1-(dimethylcarbamoyl)piperidin-4-yl)azetidin-3-yl)-1H-pyrazol-4-yl)-6-(1H-pyrazol-3-yl)-2-picolinamide

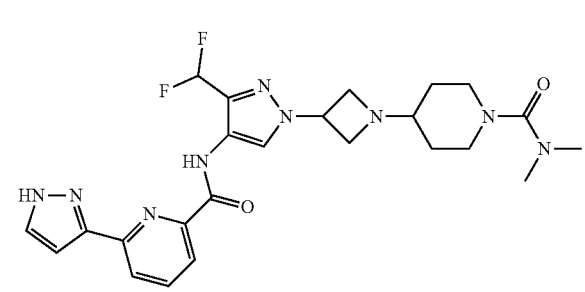

This example was prepared following the method of Example 5. LCMS (ESI): m/z=514 (M+H)+. 1H NMR (400 MHz, Chloroform-d) δ 10.46 (s, 1H), 8.50 (s, 1H), 8.15 (d, J=7.8 Hz, 1H), 8.11 (d, J=7.8 Hz, 1H), 7.96 (t, J=7.8 Hz, 1H), 7.71 (d, J=2.3 Hz, 1H), 7.02 (d, J=2.3 Hz, 1H), 6.90 (t, J=54.7 Hz, 1H), 5.04-4.94 (m, 1H), 3.89 (t, J=7.4 Hz, 2H), 3.66-3.59 (m, 2H), 3.55 (t, J=7.5 Hz, 2H), 2.89-2.78 (m, 8H), 2.47-2.38 (m, 1H), 1.81-1.72 (m, 2H), 1.42-1.29 (m, 2H).

Example 29

N-(3-(difluoromethyl)-1-(1-(1-isobutyrylpiperidin-4-yl)azetidin-3-yl)-1H-pyrazol-4-yl)-6-(1H-pyrazol-3-yl)-2-picolinamide

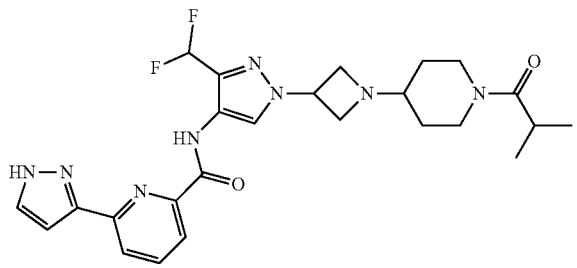 [SMILES: CC(C)C(=O)N1CCC(N2CC(n3cc(NC(=O)c4cccc(-c5cc[nH]n5)n4)c(C(F)F)n3)C2)CC1]

This example was prepared following the method of Example 5. LCMS (ESI): m/z=513 (M+H)⁺. ¹H NMR (400 MHz, Chloroform-d) δ 10.45 (s, 1H), 8.50 (s, 1H), 8.18-8.07 (m, 2H), 7.96 (t, J=7.8 Hz, 1H), 7.71 (d, J=2.3 Hz, 1H), 7.05-6.74 (m, 2H), 5.06-4.89 (m, 1H), 4.41-4.26 (m, 1H), 3.96-3.77 (m, 3H), 3.63-3.48 (m, 2H), 3.25-3.07 (m, 1H), 3.02-2.89 (m, 1H), 2.87-2.74 (m, 1H), 2.60-2.45 (m, 1H), 1.86-1.66 (m, 2H), 1.44-1.20 (m, 2H), 1.13 (d, J=6.8 Hz, 6H).

Example 30

(S)—N-(3-(difluoromethyl)-1-(1-(1-(2-hydroxypropionyl)piperidin-4-yl)azetidin-3-yl)-1H-pyrazol-4-yl)-6-(1-(2,2,2-trifluoroethyl)-1H-pyrazol-4-yl)-2-picolinamide

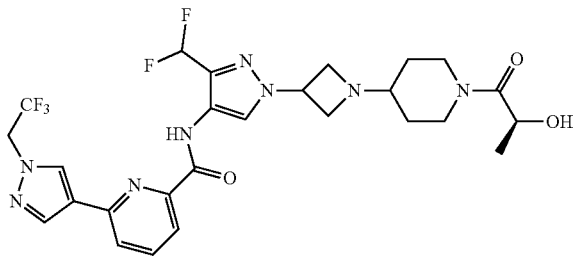 [SMILES: C[C@H](O)C(=O)N1CCC(N2CC(n3cc(NC(=O)c4cccc(-c5cnn(CC(F)(F)F)c5)n4)c(C(F)F)n3)C2)CC1]

This example was prepared following the method of Example 4. LCMS (ESI): m/z=597 (M+H)⁺. ¹H NMR (400 MHz, Chloroform-d) δ 10.48 (s, 1H), 8.50 (s, 1H), 8.13 (s, 1H), 8.12 (s, 1H), 8.07 (d, J=7.7 Hz, 1H), 7.91 (t, J=7.8 Hz, 1H), 7.67 (d, J=8.1 Hz, 1H), 6.89 (t, J=54.6 Hz, 1H), 5.01-4.91 (m, 1H), 4.81 (q, J=8.3 Hz, 2H), 4.51-4.42 (m, 1H), 4.26-4.12 (m, 1H), 3.94-3.81 (m, 3H), 3.72-3.63 (m, 1H), 3.59-3.49 (m, 2H), 3.23-3.09 (m, 2H), 2.59-2.48 (m, 1H), 1.84-1.72 (m, 2H), 1.44-1.35 (m, 2H), 1.33 (d, J=6.6 Hz, 3H).

Example 31

(R)—N-(3-(difluoromethyl)-1-(1-(1-(2-hydroxypropionyl)piperidin-4-yl)azetidin-3-yl)-1H-pyrazol-4-yl)-6-(1-(2,2,2-trifluoroethyl)-1H-pyrazol-4-yl)-2-picolinamide

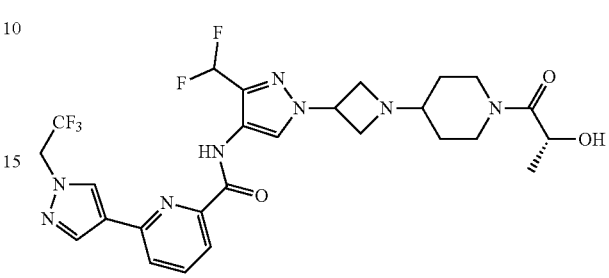

This example was prepared following the method of Example 4. LCMS (ESI): m/z=597 (M+H)⁺. ¹H NMR (400 MHz, Chloroform-d) δ 10.48 (s, 1H), 8.50 (s, 1H), 8.12 (s, 1H), 8.11 (s, 1H), 8.07 (d, J=7.5 Hz, 1H), 7.91 (t, J=7.8 Hz, 1H), 7.66 (d, J=7.9 Hz, 1H), 6.88 (t, J=54.6 Hz, 1H), 5.01-4.89 (m, 1H), 4.80 (q, J=8.3 Hz, 2H), 4.52-4.41 (m, 1H), 4.25-4.11 (m, 1H), 3.90 (s, 1H), 3.84 (t, J=7.4 Hz, 2H), 3.71-3.61 (m, 1H), 3.58-3.47 (m, 2H), 3.25-3.08 (m, 2H), 2.59-2.46 (m, 1H), 1.85-1.72 (m, 2H), 1.44-1.35 (m, 2H), 1.32 (d, J=6.5 Hz, 3H).

Example 32

N-(3-(difluoromethyl)-1-(1-(1-(2-hydroxy-2-methylpropionyl)piperidin-4-yl)azetidin-3-yl)-1H-pyrazol-4-yl)-6-(1-(2,2,2-trifluoroethyl)-1H-pyrazol-4-yl)-2-picolinamide

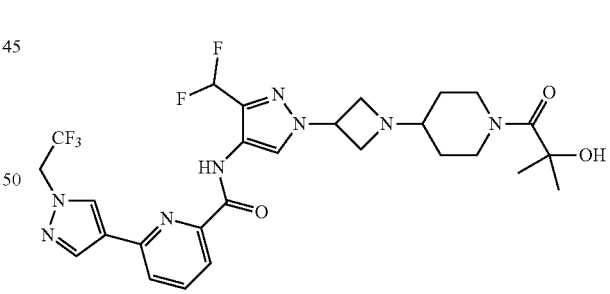

This example was prepared following the method of Example 4. LCMS (ESI): m/z=611 (M+H)⁺. ¹H NMR (400 MHz, Chloroform-d) δ 10.48 (s, 1H), 8.50 (s, 1H), 8.12 (s, 1H), 8.12 (s, 1H), 8.07 (d, J=7.6 Hz, 1H), 7.91 (t, J=7.8 Hz, 1H), 7.66 (d, J=7.8 Hz, 1H), 6.89 (t, J=54.6 Hz, 1H), 5.01-4.91 (m, 1H), 4.80 (q, J=8.4 Hz, 2H), 4.61 (s, 1H), 4.23-4.07 (m, 2H), 3.84 (t, J=7.8 Hz, 2H), 3.53 (t, J=7.5 Hz, 2H), 3.26-3.13 (m, 2H), 2.57-2.48 (m, 1H), 1.82-1.74 (m, 2H), 1.50 (s, 6H), 1.37 (s, 2H).

Example 33

N-(3-(difluoromethyl)-1-(1-(1-(methylsulfonyl)piperidin-4-yl)azetidin-3-yl)-1H-pyrazol-4-yl)-6-(1-(2,2,2-trifluoroethyl)-1H-pyrazol-4-yl)-2-picolinamide

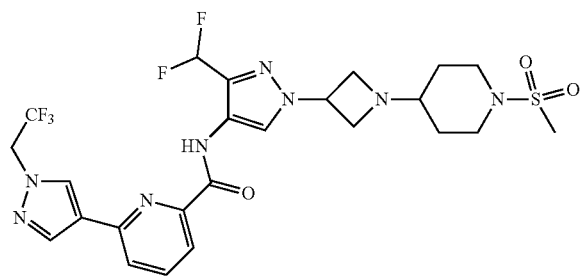 [SMILES: CS(=O)(=O)N1CCC(N2CC(n3cc(NC(=O)c4cccc(-c5cnn(CC(F)(F)F)c5)n4)c(C(F)F)n3)C2)CC1]

This example was prepared following the method of Example 4. LCMS (ESI): m/z=603 (M+H)+. 1H NMR (400 MHz, Chloroform-d) δ 10.48 (s, 1H), 8.52 (s, 1H), 8.13 (s, 1H), 8.11 (s, 1H), 8.06 (d, J=7.8 Hz, 1H), 7.91 (t, J=7.8 Hz, 1H), 7.66 (d, J=7.9 Hz, 1H), 6.88 (t, J=54.6 Hz, 1H), 4.99-4.89 (m, 1H), 4.80 (q, J=8.3 Hz, 2H), 3.81 (t, J=7.7 Hz, 2H), 3.59-3.46 (m, 4H), 3.08-2.98 (m, 2H), 2.82 (s, 3H), 2.48-2.40 (m, 1H), 1.88-1.77 (m, 2H), 1.58-1.46 (m, 2H).

Example 34

(S)-6-(1-(2,2-difluoroethyl)-1H-pyrazol-4-yl)-N-(3-(difluoromethyl)-1-(1-(1-(2-hydroxypropionyl)piperidin-4-yl)azetidin-3-yl)-1H-pyrazol-4-yl)-2-picolinamide

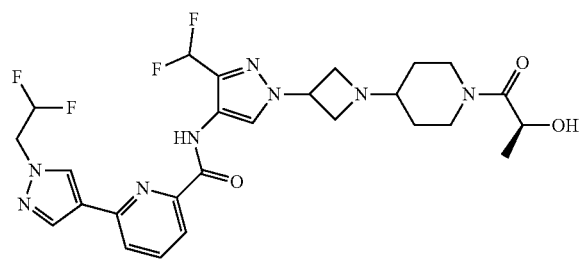 [SMILES: C[C@H](O)C(=O)N1CCC(N2CC(n3cc(NC(=O)c4cccc(-c5cnn(CC(F)F)c5)n4)c(C(F)F)n3)C2)CC1]

This example was prepared following the method in step 3 in Example 2. LCMS (ESI): m/z=579 (M+H)+. 1H NMR (400 MHz, Chloroform-d) δ 10.48 (s, 1H), 8.50 (s, 1H), 8.11 (s, 1H), 8.08-8.02 (m, 2H), 7.89 (t, J=7.8 Hz, 1H), 7.64 (d, J=7.9 Hz, 1H), 6.89 (t, J=54.7 Hz, 1H), 6.16 (tt, J=55.4, 4.3 Hz, 1H), 5.01-4.90 (m, 1H), 4.56 (td, J=13.5, 4.2 Hz, 2H), 4.50-4.41 (m, 1H), 4.25-4.10 (m, 1H), 3.90 (s, 1H), 3.83 (t, J=7.4 Hz, 2H), 3.72-3.61 (m, 1H), 3.59-3.47 (m, 2H), 3.25-3.08 (m, 2H), 2.59-2.47 (m, 1H), 1.84-1.71 (m, 2H), 1.43-1.34 (m, 2H), 1.32 (d, J=6.4 Hz, 3H).

Example 35

(R)-6-(1-(2,2-difluoroethyl)-1H-pyrazol-4-yl)-N-(3-(difluoromethyl)-1-(1-(1-(2-hydroxypropionyl)piperidin-4-yl)azetidin-3-yl)-1H-pyrazol-4-yl)-2-picolinamide

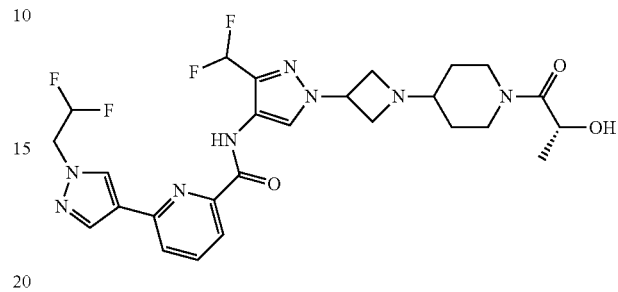

This example was prepared following the method in step 3 in Example 2. LCMS (ESI): m/z=579 (M+H)+. 1H NMR (400 MHz, Chloroform-d) δ 10.48 (s, 1H), 8.50 (s, 1H), 8.11 (s, 1H), 8.08-8.02 (m, 2H), 7.89 (t, J=7.8 Hz, 1H), 7.64 (d, J=7.8 Hz, 1H), 6.89 (t, J=54.6 Hz, 1H), 6.16 (tt, J=55.3, 4.2 Hz, 1H), 5.01-4.91 (m, 1H), 4.56 (td, J=13.5, 4.3 Hz, 2H), 4.46 (q, J=6.5 Hz, 1H), 4.24-4.11 (m, 1H), 3.84 (t, J=7.4 Hz, 2H), 3.72-3.61 (m, 1H), 3.57-3.48 (m, 2H), 3.23-3.08 (m, 2H), 2.58-2.48 (m, 1H), 1.83-1.70 (m, 2H), 1.44-1.34 (m, 2H), 1.32 (d, J=6.5 Hz, 3H).

Example 36

6-(1-(2,2-Difluoroethyl)-1H-pyrazol-4-yl)-N-(3-(difluoromethyl)-1-(1-(1-(2-hydroxy-2-methylpropionyl)piperidin-4-yl)azetidin-3-yl)-1H-pyrazol-4-yl)-2-picolinamide

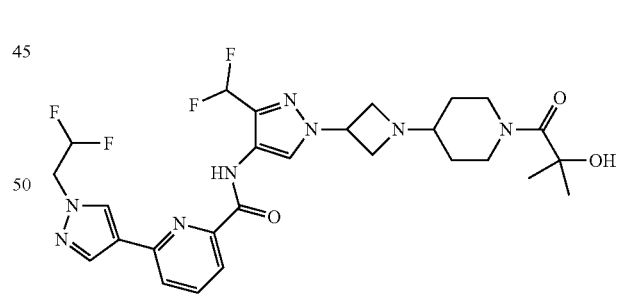

This example was prepared following the method in step 3 in Example 2. LCMS (ESI): m/z=593 (M+H)+. 1H NMR (400 MHz, Chloroform-d) δ 10.49 (s, 1H), 8.51 (s, 1H), 8.11 (s, 1H), 8.08-8.02 (m, 2H), 7.89 (t, J=7.8 Hz, 1H), 7.65 (d, J=7.8 Hz, 1H), 6.89 (t, J=54.6 Hz, 1H), 6.16 (tt, J=55.3, 4.2 Hz, 1H), 5.02-4.90 (m, 1H), 4.67-4.50 (m, 3H), 4.23-4.07 (m, 2H), 3.84 (t, J=7.7 Hz, 2H), 3.54 (t, J=7.5 Hz, 2H), 3.25-3.14 (m, 2H), 2.57-2.49 (m, 1H), 1.82-1.74 (m, 2H), 1.50 (s, 6H), 1.42-1.30 (m, 2H).

Example 37

6-(1-(2,2-Difluoroethyl)-1H-pyrazol-4-yl)-N-(3-(difluoromethyl)-1-(1-(1-(methylsulfonyl)piperidin-4-yl)azetidin-3-yl)-1H-pyrazol-4-yl)-2-picolinamide

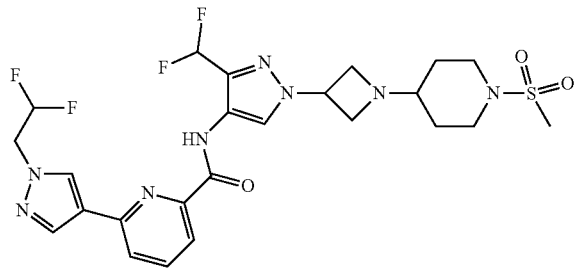 [SMILES: CS(=O)(=O)N1CCC(N2CC(n3cc(NC(=O)c4cccc(-c5cnn(CC(F)F)c5)n4)c(C(F)F)n3)C2)CC1]

This example was prepared following the method of Example 33. LCMS (ESI): m/z=585 (M+H)⁺. ¹H NMR (400 MHz, Chloroform-d) δ 10.48 (s, 1H), 8.52 (s, 1H), 8.11 (s, 1H), 8.06 (s, 1H), 8.04 (d, J=7.6 Hz, 1H), 7.89 (t, J=7.8 Hz, 1H), 7.64 (d, J=7.8 Hz, 1H), 6.89 (t, J=54.6 Hz, 1H), 6.16 (tt, J=55.3, 4.2 Hz, 1H), 5.03-4.89 (m, 1H), 4.56 (td, J=13.5, 4.3 Hz, 2H), 3.85 (t, J=7.4 Hz, 2H), 3.61-3.48 (m, 4H), 3.10-2.97 (m, 2H), 2.82 (s, 3H), 2.54-2.43 (m, 1H), 1.88-1.78 (m, 2H), 1.59-1.47 (m, 2H).

Example 38

6-(1-(2,2-Difluoroethyl)-1H-pyrazol-4-yl)-N-(3-(difluoromethyl)-1-(1-(1-(dimethylcarbamoyl)piperidin-4-yl)azetidin-3-yl)-1H-pyrazol-4-yl)-2-picolinamide

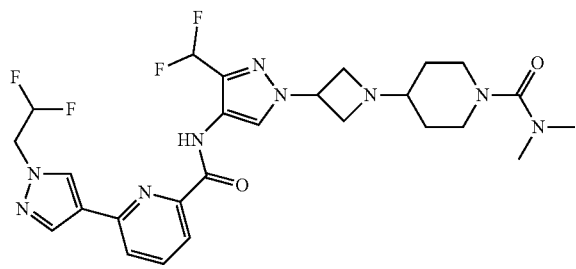 [SMILES: CN(C)C(=O)N1CCC(N2CC(n3cc(NC(=O)c4cccc(-c5cnn(CC(F)F)c5)n4)c(C(F)F)n3)C2)CC1]

This example was prepared following the methods in steps 1 and 2 in Example 17 and step 3 in Example 2. LCMS (ESI): m/z=578 (M+H)⁺. ¹H NMR (400 MHz, Chloroform-d) δ 10.47 (s, 1H), 8.49 (s, 1H), 8.10 (s, 1H), 8.07-8.02 (m, 2H), 7.89 (t, J=7.8 Hz, 1H), 7.64 (d, J=7.8 Hz, 1H), 6.89 (t, J=54.6 Hz, 1H), 6.16 (tt, J=55.3, 4.2 Hz, 1H), 5.01-4.92 (m, 1H), 4.55 (td, J=13.5, 4.3 Hz, 2H), 3.85 (t, J=7.6 Hz, 2H), 3.64-3.56 (m, 2H), 3.53 (t, J=7.4 Hz, 2H), 2.90-2.75 (m, 8H), 2.45-2.33 (m, 1H), 1.81-1.69 (m, 2H), 1.42-1.26 (m, 2H).

Example 39

(S)—N-(3-(difluoromethyl)-1-(1-(1-(2-hydroxypropionyl)piperidin-4-yl)azetidin-3-yl)-1H-pyrazol-4-yl)-6-(1H-pyrazol-3-yl)-2-picolinamide

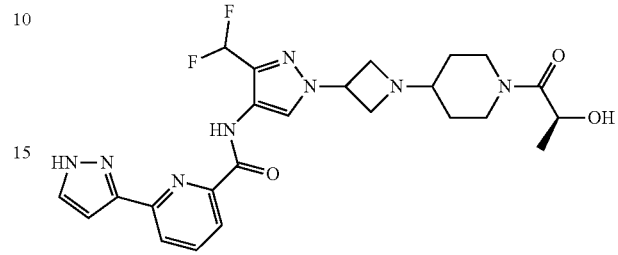

This example was prepared following the method of Example 5. LCMS (ESI): m/z=515 (M+H)⁺. ¹H NMR (400 MHz, Chloroform-d) δ 10.45 (s, 1H), 8.51 (s, 1H), 8.16 (d, J=7.7 Hz, 1H), 8.11 (d, J=7.8 Hz, 1H), 7.96 (t, J=7.8 Hz, 1H), 7.70 (d, J=2.3 Hz, 1H), 7.02 (d, J=2.3 Hz, 1H), 6.90 (t, J=54.7 Hz, 1H), 5.01-4.90 (m, 1H), 4.52-4.41 (m, 1H), 4.24-4.11 (m, 1H), 3.93 (s, 1H), 3.84 (t, J=7.5 Hz, 2H), 3.72-3.60 (m, 1H), 3.58-3.47 (m, 2H), 3.24-3.08 (m, 2H), 2.59-2.46 (m, 1H), 1.84-1.71 (m, 2H), 1.43-1.28 (m, 5H).

Example 40

(R)—N-(3-(difluoromethyl)-1-(1-(1-(2-hydroxypropionyl)piperidin-4-yl)azetidin-3-yl)-1H-pyrazol-4-yl)-6-(1H-pyrazol-3-yl)-2-picolinamide

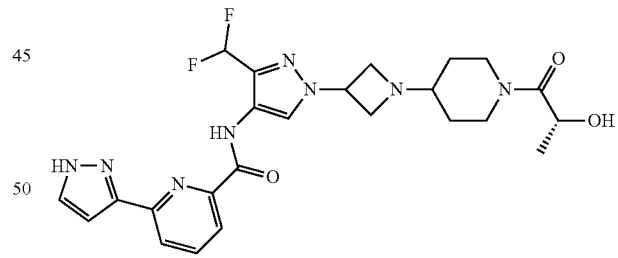

This example was prepared following the method of Example 5. LCMS (ESI): m/z=515 (M+H)⁺. ¹H NMR (400 MHz, Chloroform-d) δ 10.45 (s, 1H), 8.51 (s, 1H), 8.16 (d, J=7.8 Hz, 1H), 8.11 (d, J=7.8 Hz, 1H), 7.96 (t, J=7.8 Hz, 1H), 7.70 (d, J=2.3 Hz, 1H), 7.02 (d, J=2.3 Hz, 1H), 6.90 (t, J=54.7 Hz, 1H), 5.03-4.89 (m, 1H), 4.54-4.41 (m, 1H), 4.27-4.09 (m, 1H), 3.94 (s, 1H), 3.84 (t, J=7.4 Hz, 2H), 3.72-3.61 (m, 1H), 3.59-3.47 (m, 2H), 3.26-3.08 (m, 2H), 2.59-2.46 (m, 1H), 1.87-1.71 (m, 2H), 1.44-1.27 (m, 5H).

Example 41

N-(3-(difluoromethyl)-1-(1-(1-(2-hydroxy-2-methyl-propionyl)piperidin-4-yl)azetidin-3-yl)-1H-pyrazol-4-yl)-6-(1H-pyrazol-3-yl)-2-picolinamide

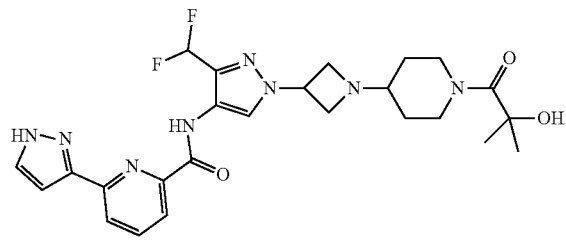 [SMILES: CC(C)(O)C(=O)N1CCC(N2CC(n3cc(NC(=O)c4cccc(-c5cc[nH]n5)n4)c(C(F)F)n3)C2)CC1]

This example was prepared following the method of Example 5. LCMS (ESI): m/z=529 (M+H)$^+$. $^1$H NMR (400 MHz, Chloroform-d) δ 10.45 (s, 1H), 8.51 (s, 1H), 8.16 (dd, J=7.6, 1.1 Hz, 1H), 8.11 (d, J=7.9 Hz, 1H), 7.96 (t, J=7.7 Hz, 1H), 7.70 (d, J=2.3 Hz, 1H), 7.02 (d, J=2.3 Hz, 1H), 6.90 (t, J=54.7 Hz, 1H), 5.01-4.91 (m, 1H), 4.63 (s, 1H), 4.27-4.04 (m, 2H), 3.84 (t, J=7.8 Hz, 2H), 3.54 (t, J=7.6 Hz, 2H), 3.28-3.11 (m, 2H), 2.58-2.47 (m, 1H), 1.83-1.73 (m, 2H), 1.50 (s, 6H), 1.42-1.29 (m, 2H).

Example 42

N-(3-(difluoromethyl)-1-(1-(1-(methylsulfonyl)piperidin-4-yl)azetidin-3-yl)-1H-pyrazol-4-yl)-6-(1H-pyrazol-3-yl)-2-picolinamide

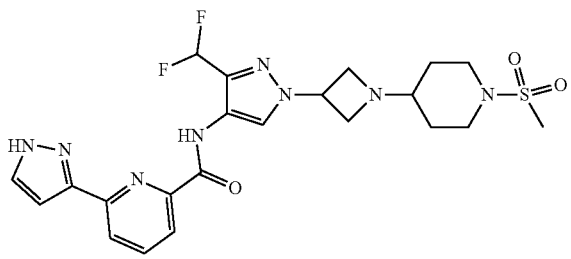 [SMILES: CS(=O)(=O)N1CCC(N2CC(n3cc(NC(=O)c4cccc(-c5cc[nH]n5)n4)c(C(F)F)n3)C2)CC1]

This example was prepared following the method of Example 5. LCMS (ESI): m/z=521 (M+H)$^+$. $^1$H NMR (400 MHz, Chloroform-d) δ 10.45 (s, 1H), 8.53 (s, 1H), 8.15 (d, J=7.6 Hz, 1H), 8.11 (d, J=7.8 Hz, 1H), 7.97 (t, J=7.8 Hz, 1H), 7.71 (d, J=2.4 Hz, 1H), 7.06-6.72 (m, 2H), 5.04-4.90 (m, 1H), 3.83 (t, J=7.4 Hz, 2H), 3.60-3.43 (m, 4H), 3.11-2.97 (m, 2H), 2.82 (s, 3H), 2.53-2.40 (m, 1H), 1.89-1.78 (m, 2H), 1.59-1.48 (m, 2H).

Example 43

6-(1-(2-Cyanopropan-2-yl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide

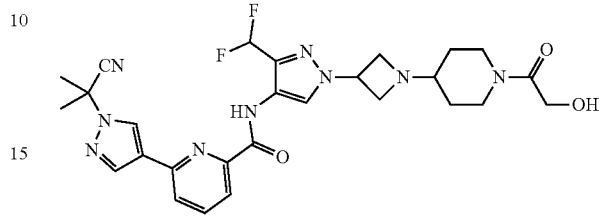

This example was prepared following the method of Example 12. LCMS (ESI): m/z=568 (M+H)$^+$. $^1$H NMR (400 MHz, Chloroform-d) δ 10.52 (s, 1H), 8.49 (s, 1H), 8.29 (s, 1H), 8.13 (s, 1H), 8.05 (dd, J=7.5, 1.1 Hz, 1H), 7.90 (t, J=7.8 Hz, 1H), 7.66 (dd, J=7.9, 1.1 Hz, 1H), 6.88 (t, J=54.6 Hz, 1H), 5.08-4.91 (m, 1H), 4.27-4.09 (m, 3H), 3.98-3.79 (m, 2H), 3.66-3.44 (m, 3H), 3.27-2.94 (m, 2H), 2.67-2.47 (m, 1H), 2.08 (s, 6H), 1.87-1.68 (m, 2H), 1.48-1.33 (m, 2H).

Test Example A: IRAK4 Kinase Activity Assay

Inhibitory activity (IC$_{50}$) of the compounds against IRAK4 kinase under Km ATP was detected through mobility spectrum analysis (MSA). IRAK4 kinase was purchased from Carna (Cat. No.: 09-145, batch No.: 14CBS-0020H), and Kinase Substrate 8 was purchased from GL Biochem (Cat. No.: 112396, batch No.: P171207-MJI112396).

The compounds were prepared with DMSO to 100 times the final reaction concentration and diluted to 10 concentrations in sequence at a 3-fold dilution ratio starting from 1 μM. Then 0.25 μL was transferred to a 384-well plate using Echo550. A 1× kinase buffer (50 mM HEPES, pH=7.5, 0.0015% Brij-35, 10 mM MgCl$_2$, 2 mM DTT) was used to prepare a kinase solution of 2.5 times the final concentration. Then 10 μL of the kinase solution of 2.5 times the final concentration was added to each compound well, shaken and mixed uniformly, and incubated at room temperature for 10 min. A 1× kinase buffer was used to prepare a mixed solution of ATP and substrate Kinase Substrate 8 with a concentration of 25/15 times the final concentration. 15 μL of the mixed solution of ATP and the substrate with a concentration of 25/15 times the final concentration were added to each well (the final concentration of IRAK4 kinase was 1 nM, the final concentration of the substrate was 3 μM, and the final concentration of ATP was 15.6 μM), shaken and mixed uniformly, and reacted at room temperature for 60 min. Finally, 30 μL of stopping solution (100 mM HEPES, pH=7.5, 0.0015% Brij-35, 0.2% Coating Reagent #3, 50 mM EDTA) was added to terminate the reaction. CaliperEZ Reader II was used to read data about conversion rates that was then converted into data about inhibition rates. According to the data about the inhibition rate at each concentration, the half maximal inhibitory concentration (IC$_{50}$) (Table 1) was calculated by a Logit method.

TABLE 1

Activity of the compounds of the present application in inhibiting IRAK4 kinase

| Example | IRAK4 IC$_{50}$ (nM) |
|---|---|
| 1 | 1.2 |
| 2 | 0.99 |
| 3 | 0.87 |
| 4 | 0.68 |
| 5 | 4.3 |
| 6 | 4.2 |
| 7 | 3.3 |
| 8 | 1.9 |
| 9 | 2.5 |
| 10 | 2.0 |
| 11 | 1.6 |
| 12 | 0.91 |
| 13 | 0.73 |
| 14 | 3.2 |
| 15 | 3.9 |
| 16 | 1.8 |
| 17 | 0.57 |
| 18 | 0.67 |
| 19 | 1.9 |
| 20 | 3.2 |
| 21 | 1.7 |
| 22 | 2.5 |
| 23 | 0.63 |
| 24 | 0.59 |
| 25 | 0.65 |
| 26 | 0.54 |
| 27 | 0.51 |
| 28 | 0.68 |
| 29 | 0.81 |
| 30 | 3.3 |
| 31 | 0.79 |
| 32 | 0.97 |
| 33 | 4.9 |
| 34 | 1.0 |
| 35 | 1.3 |
| 36 | 0.96 |
| 37 | 5.8 |
| 38 | 1.5 |
| 39 | 0.69 |
| 40 | 0.59 |
| 41 | 0.43 |
| 42 | 1.2 |
| 43 | 0.97 |
| Staurosporine | 33 |

Test Example B: Cellular Activity Assay

Inhibition of IRAK4 by the compounds of the present application was evaluated in THP-1 cells for cellular activity. The stimulus used in this experiment was LPS. LPS is a TLR4 agonist that stimulates the secretion of TNFα through TLR-IRAK4 signaling pathway in the THP-1 cells. Once the signaling pathway is inhibited by IRAK4 inhibitors, the production of TNFα is inhibited. In this experiment, the secretion of TNFα was detected by ELISA.

150 μL of RPMI-1640 medium (Gibco, catalog No.: 11875-085) solution containing 10000 THP-1 cells were added to each well of a 96-well plate and then 25 μL of a test compound solution of 8 times the final concentration (starting from 10 PM, 3-fold dilution, 8 concentrations, each concentration containing 4% DMSO RPMI-1640 medium) were added, and they were mixed uniformly and incubated at 37° C. for 30 min. 25 μL of RPMI-1640 medium solution containing LPS were added to each well (the final LPS concentration was 1 μg/mL and the final DMSO concentration was 0.5%), mixed uniformaly, and incubated at 37° C. for 4.5 h. The 96-well plate was rotated at 2000 rpm for 5 min, then 50 μL of supernatant was taken, and the TNFα content in the supernatant was determined with a human ELISA kit (Life Technologies, catalog No.: KHC3011). The IC$_{50}$ (Table 2) of the compound was calculated by XL-Fit.

TABLE 2

Activity of compounds of the present application in inhibiting TNFα secretion in THP-1 cells simulated by LPS

| Example | IC$_{50}$ (nM) |
|---|---|
| 1 | 29 |
| 2 | 27 |
| 3 | 35 |
| 4 | 33 |
| 12 | 43 |
| 13 | 25 |
| 24 | 20 |
| 27 | 18 |
| 31 | 42 |
| 32 | 52 |
| 34 | 46 |
| 35 | 48 |
| 36 | 50 |
| 40 | 26 |
| 41 | 23 |
| 43 | 42 |

The results in Table 1 and Table 2 show that the compounds of the present application can effectively inhibit the activity of IRAK4 kinase and can also effectively inhibit LPS-stimulated TNFα secretion in THP-1 cells.

What is claimed is:

1. A compound represented by Formula (I) or a pharmaceutically acceptable salt thereof, wherein the compound represented by Formula (I) has the following structure:

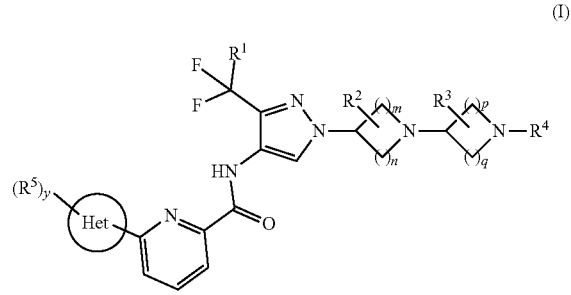

(I)

wherein the Het ring is a five- or six-membered heteroaromatic ring;

$R^1$ is selected from H or D;

$R^2$ and $R^3$ are each selected from H, D, alkyl, halogen, or $OR^a$;

$R^4$ is selected from $COR^d$, $CONR^bR^c$, $CO_2R^d$, $SO_2R^d$, or $SO_2NR^bR^c$;

$R^5$ is selected from H, D, halogen, cyano, $OR^a$, $SR^a$, $NR^bR^c$, $COR^d$, $CONR^bR^c$, $CO_2R^d$, $SO_2R^d$, $SO_2NR^bR^c$, alkyl, alkenyl, alkynyl, cycloalkyl, or heterocycloalkyl; wherein the alkyl, alkenyl, alkynyl, cycloalkyl, or heterocycloalkyl is unsubstituted or substituted with 1 to 3 $R^{5a}$;

$R^{5a}$ is selected from H, D, halogen, cyano, alkyl, alkenyl, alkynyl, cycloalkyl, heterocycloalkyl, $OR^a$, $SR^a$, $NR^bR^c$, $COR^d$, $CONR^bR^c$, $CO_2R^d$, $SO_2R^d$, or $SO_2NR^bR^c$; wherein the alkyl, cycloalkyl, or heterocycloalkyl is unsubstituted or substituted with 1 to 3 $R^{5b}$;

$R^{5b}$ is selected from H, D, halogen, cyano, $OR^a$, $SR^a$, $NR^bR^c$, $COR^d$, $CONR^bR^c$, $CO_2R^d$, $SO_2R^d$, or $SO_2NR^bR^c$;

$R^a$, $R^b$, $R^c$, and $R^d$ are each selected from H, D, alkyl, alkenyl, alkynyl, cycloalkyl, heterocycloalkyl, aryl, or heteroaryl, wherein the alkyl, alkenyl, alkynyl, cycloalkyl, heterocycloalkyl, aryl, or heteroaryl is unsubstituted or substituted with 1 to 4 $R^6$;

$R^6$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl;

wherein $R^b$ and $R^c$ in a group containing both $R^b$ and $R^c$ are attached to a N atom in the group by a single bond or form a heterocycloalkyl together with the N atom to which they are attached, and the heterocycloalkyl is unsubstituted or substituted with 1 to 3 $R^7$;

$R^7$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl; and m, n, p, q, and y are each independently 1, 2, or 3.

2. The compound or the pharmaceutically acceptable salt thereof according to claim 1, wherein the compound has a structure represented by Formula (IA):

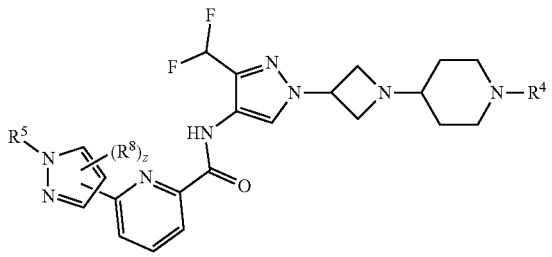

(IA)

wherein $R^4$ is selected from $COR^d$, $CONR^bR^c$, $CO_2R^d$, $SO_2R^d$, or $SO_2NR^bR^c$;

$R^5$ is selected from H, D, halogen, cyano, $OR^a$, $SR^a$, $NR^bR^c$, $COR^d$, $CONR^bR^c$, $CO_2R^d$, $SO_2R^d$, $SO_2NR^bR^c$, alkyl, alkenyl, alkynyl, cycloalkyl, or heterocycloalkyl; wherein the alkyl, alkenyl, alkynyl, cycloalkyl, or heterocycloalkyl is unsubstituted or substituted with 1 to 3 $R^{5a}$;

$R^{5a}$ is selected from H, D, halogen, cyano, alkyl, alkenyl, alkynyl, cycloalkyl, heterocycloalkyl, $OR^a$, $SR^a$, $NR^bR^c$, $COR^d$, $CONR^bR^c$, $CO_2R^d$, $SO_2R^d$, or $SO_2NR^bR^c$; wherein the alkyl, cycloalkyl, and heterocycloalkyl are unsubstituted or substituted with 1 to 3 $R^{5b}$;

$R^{5b}$ is selected from H, D, halogen, cyano, $OR^a$, $SR^a$, $NR^bR^c$, $COR^d$, $CONR^bR^c$, $CO_2R^d$, $SO_2R^d$, or $SO_2NR^bR^c$;

$R^8$ is selected from H, D, alkyl, halogen, haloalkyl, or $OR^a$;

$R^a$, $R^b$, $R^c$, and $R^d$ are each selected from H, D, alkyl, alkenyl, alkynyl, cycloalkyl, heterocycloalkyl, aryl, or heteroaryl, wherein the alkyl, alkenyl, alkynyl, cycloalkyl, heterocycloalkyl, aryl, or heteroaryl is unsubstituted or substituted with 1 to 4 $R^6$;

$R^6$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl;

wherein $R^b$ and $R^c$ in a group containing both $R^b$ and $R^c$ are attached to a N atom in the group by a single bond or form a heterocycloalkyl together with the N atom to which they are attached, and the heterocycloalkyl is unsubstituted or substituted with 1 to 3 $R^7$;

$R^7$ is selected from H, D, halogen, cyano, $OR^a$, $SR^a$, $NR^bR^c$, $NR^bCOR^d$, $NR^bCONR^bR^c$, $CONR^bR^c$, $CO_2R^d$, $NR^bSO_2R^d$, $NR^bSO_2NR^bR^c$, $SOR^d$, $SO_2R^d$, $SO_2NR^bR^c$, alkyl, cycloalkyl, heterocycloalkyl, aryl, or heteroaryl; and z is 1 or 2.

3. The compound or the pharmaceutically acceptable salt thereof according to claim 1, wherein the compound is selected from the group consisting of:

N-(1-(1-(1-acetylpiperidin-4-yl)azetidin-3-yl)-3-(difluoromethyl)-1H-pyrazol-4-yl)-6-(1-(2,2-difluoroethyl)-1H-pyrazol-4-yl)-2-picolinamide, 6-(1-(2,2-difluoroethyl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(2,2,2-trifluoroethyl)-1H-pyrazol-4-yl)-2-picolinamide, N-(3-(difluoromethyl)-1-(1-(1-(2-hydroxyacetyl)piperidin-4-yl)azetidin-3-yl)-1H-pyrazol-4-yl)-6-(1-(2,2,2-trifluoroethyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(difluoromethyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-methyl-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-ethyl-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-isopropyl-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(1-cyanocyclopropyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(1-cyanocyclobutyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(1-(aminomethyl)cyclobutyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(2-cyanopropan-2-yl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(1-amino-2-methylpropan-2-yl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(1-(hydroxymethyl)cyclobutyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(2-hydroxy-2-methylpropyl)-1H-pyrazol-4-yl)-2-picolinamide, N-(1-(1-(1-acetylpiperidin-4-yl)azetidin-3-yl)-3-(difluoromethyl)-1H-pyrazol-4-yl)-6-(1-(1-hydroxy-2-methylpropyl-2-yl)-1H-pyrazol-4-yl)-2-picolinamide, 6-(1-(1-amino-2-methylpropan-2-yl)-1H-pyrazol-4-yl)-N-(3-(difluoromethyl)-1-(1-(1-(dimethylcarbamoyl)piperidin-4-yl)azetidin-3-yl)-1H-pyrazol-4-yl)-2-picolinamide, methyl 4-(3-(4-(6-(1-(1-amino-2-methylpropan-2-yl)-1H-pyrazol-4-yl)-2-picolinamide)-3-(difluoromethyl)-1H-pyrazol-1-yl)azetidin-1-yl)piperidine-1-carboxylate, N-(1-(1-(1-acetylpiperidin-4-yl)azetidin-3-yl)-3-(difluoromethyl)-1H-pyrazol-4-yl)-6-(1H-pyrazol-4-yl)-2-picolinamide, N-(3-(difluoromethyl)-1-(1-(1-(dimethylcarbamoyl)piperidin-4-yl)azetidin-3-yl)-1H-pyrazol-4-yl)-6-(1H-pyrazol-4-yl)-2-picolinamide, methyl 4-(3-(4-(6-(1H-pyrazol-4-yl)-2-picolinamide)-3-(difluoromethyl)-1H-pyrazol-1-yl)azetidin-1-yl)piperidine-1-carboxylate, N-(1-(1-(1-acryloylpiperidin-4-yl)azetidin-3-yl)-3-(difluoromethyl)-1H-pyrazol-4-yl)-6-(1H-pyrazol-4-yl)-2-picolinamide, N-(1-(1-(1-acryloylpiperidin-4-yl)azetidin-3-yl)-3-(difluoromethyl)-1H-pyrazol-4-yl)-6-(1H-pyrazol-3-yl)-2-picolinamide, N-(1-(1-(1-acetylpiperidin-4-yl)azetidin-3-yl)-3-(difluoromethyl)-1H-pyrazol-4-yl)-6-(1H-pyrazol-3-yl)-2-picolinamide, methyl 4-(3-(4-(6-(1H-pyrazol-3-yl)-2-picolinamide)-3-(difluoromethyl)-1H-pyrazol-1-yl)azetidin-1-yl)piperidine-1-carboxylate, N-(3-(difluoromethyl)-1-(1-(1-propionylpiperidin-4-yl)azetidin-3-yl)-1H-pyrazol-4-yl)-6-(1H-pyrazol-3-yl)-2-picolinamide, N-(3-(difluoromethyl)-1-(1-(1-(2-hydroxyacetyl)piperidin-4-yl)azetidin-3-yl)-1H-pyrazol-4-yl)-6-(1H-pyrazol-3-yl)-2-picolinamide, N-(3-(difluoromethyl)-1-(1-(1-(dimethylcarbamoyl)piperidin-4-yl)azetidin-3-yl)-1H-pyrazol-4-yl)-6-(1H-pyrazol-3-yl)-2-picolinamide, N-(3-(difluoromethyl)-1-(1-(1-isobutyrylpiperidin-4-yl)azetidin-3-yl)-1H-pyrazol-4-yl)-6-(1H-pyrazol-3-yl)-2-picolinamide, (S)—N-(3-(difluoromethyl)-1-(1-(1-(2-hydroxypropionyl)piperidin-4-yl)azetidin-3-yl)-1H-pyrazol-4-yl)-6-(1-(2,2,2-trifluoroethyl)-1H-pyrazol-4-yl)-2-picolinamide, (R)—N-(3-(difluoromethyl)-1-(1-(1-(2-hydroxypropionyl)piperidin-4-yl)azetidin-3-yl)-1H-pyrazol-4-yl)-6-(1-(2,2,2-trifluoroethyl)-1H-pyrazol-4-yl)-2-picolinamide, N-(3-(difluoromethyl)-1-(1-(1-(2-hydroxy-2-methylpropionyl)piperidin-4-yl)azetidin-3-yl)-1H-pyrazol-4-yl)-6-(1-(2,2,2-trifluoroethyl)-1H-pyrazol-4-yl)-2-picolinamide, N-(3-(difluoromethyl)-1-(1-(1-(methylsulfonyl)piperidin-4-yl)azetidin-3-yl)-1H-pyrazol-4-yl)-6-(1-(2,2,2-trifluoroethyl)-1H-pyrazol-4-yl)-2-picolinamide, (S)-6-(1-(2,2-difluoroethyl)-1H-pyrazol-4-yl)-N-(3-(difluoromethyl)-1-(1-(1-(2-hydroxypropionyl)piperidin-4-yl)azetidin-3-yl)-1H-pyrazol-4-yl)-2-picolinamide, (R)-6-(1-(2,2-difluoroethyl)-1H-pyrazol-4-yl)-N-(3-(difluoromethyl)-1-(1-(1-(2-hydroxypropionyl)piperidin-4-yl)azetidin-3-yl)-1H-pyrazol-4-yl)-2-picolinamide, 6-(1-(2,2-difluoroethyl)-1H-pyrazol-4-yl)-N-(3-(difluoromethyl)-1-(1-(1-(2-hydroxy-2-methylpropionyl)piperidin-4-yl)azetidin-3-yl)-1H-pyrazol-4-yl)-2-picolinamide, 6-(1-(2,2-difluoroethyl)-1H-pyrazol-4-yl)-N-(3-(difluoromethyl)-1-(1-(1-(methylsulfonyl)piperidin-4-yl)azetidin-3-yl)-1H-pyrazol-4-yl)-2-picolinamide, 6-(1-(2,2-difluoroethyl)-1H-pyrazol-4-yl)-N-(3-(difluoromethyl)-1-(1-(1-(dimethylcarbamoyl)piperidin-4-yl)azetidin-3-yl)-1H-pyrazol-4-yl)-2-picolinamide, (S)—N-(3-(difluoromethyl)-1-(1-(1-(2-hydroxypropionyl)piperidin-4-yl)azetidin-3-yl)-1H-pyrazol-4-yl)-6-(1H-pyrazol-3-yl)-2-picolinamide, (R)—N-(3-(difluoromethyl)-1-(1-(1-(2-hydroxypropionyl)piperidin-4-yl)azetidin-3-yl)-1H-pyrazol-4-yl)-6-(1H-pyrazol-3-yl)-2-picolinamide, N-(3-(difluoromethyl)-1-(1-(1-(2-hydroxy-2-methylpropionyl)piperidin-4-yl)azetidin-3-yl)-1H-pyrazol-4-yl)-6-(1H-pyrazol-3-yl)-2-picolinamide, N-(3-(difluoromethyl)-1-(1-(1-(methylsulfonyl)piperidin-4-yl)azetidin-3-yl)-1H-pyrazol-4-yl)-6-(1H-pyrazol-3-yl)-2-picolinamide and 6-(1-(2-cyanopropan-2-yl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide.

4. A pharmaceutical composition, which consists of the compound or the pharmaceutically acceptable salt thereof according to claim 1 and at least one pharmaceutically acceptable carrier or excipient.

5. A method for treating a disease mediated by IRAK4 kinase, comprising administrating to a subject in need thereof the compound or the pharmaceutically acceptable salt thereof according to claim 1.

6. The method according to claim 5, wherein the disease is selected from autoimmune diseases; inflammatory diseases; pain disorders; respiratory tract, airway and lung diseases; lung inflammation and injury; pulmonary hypertension; gastrointestinal diseases; allergic diseases; infectious diseases; trauma disorders and tissue injuries; fibrotic diseases; eye diseases; joint, muscle and bone diseases; skin diseases; kidney diseases; hematopoietic diseases; liver diseases; oral diseases; metabolic disorders and heart diseases; vascular diseases; neuroinflammatory diseases; neurodegenerative diseases; sepsis; genetic disorders; and cancer.

7. The method according to claim 6, wherein the autoimmune diseases and the inflammatory diseases are selected from systemic lupus erythematosus, lupus nephritis, arthritis, psoriasis, colitis, Crohn's disease, atopic dermatitis, liver fibrosis, Alzheimer's disease, gout, cryopyrin-associated periodic syndrome, chronic kidney disease or acute kidney injury, chronic obstructive pulmonary disease, asthma, bronchi spasms, and graft-versus-host disease; and the cancer is selected from breast cancer, small cell lung cancer, non-small cell lung cancer, bronchi alveolar cancer, prostate cancer, cholangiocarcinoma, bone cancer, bladder cancer, head and neck cancer, renal cancer, liver cancer, gastrointestinal tissue cancer, esophageal cancer, ovarian cancer, pancreatic cancer, skin cancer, testicular cancer, thyroid cancer, uterine cancer, cervical and vaginal cancer, leukemia, multiple myeloma, and lymphoma.

8. The method according to claim 5, wherein the compound or the pharmaceutically acceptable salt thereof is used alone or in combination with additional medicaments; wherein the additional medicaments are any one or a combination of at least two of a small molecule medicament, a monoclonal antibody medicament, a fusion protein medicament, and an anti-sense DNA medicament.

9. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-(2,2-difluoroethyl)-1H-pyrazol-4-yl)-2-picolinamide.

10. The compound or the pharmaceutically acceptable salt thereof according to claim 1, wherein the compound is 6-(1-(2,2-difluoroethyl)-1H-pyrazol-4-yl)-N-(3-(difluoromethyl)-1-(1-(1-(2-hydroxyacetyl)piperidin-4-yl)azetidin-3-yl)-1H-pyrazol-4-yl)-2-picolinamide.

11. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-(2,2,2-trifluoroethyl)-1H-pyrazol-4-yl)-2-picolinamide.

12. The compound or the pharmaceutically acceptable salt thereof according to claim 1, wherein the compound is N-(3-(difluoromethyl)-1-(1-(1-(2-hydroxyacetyl)piperidin-4-yl)azetidin-3-yl)-1H-pyrazol-4-yl)-6-(1-(2,2,2-trifluoroethyl)-1H-pyrazol-4-yl)-2-picolinamide.

13. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-(difluoromethyl)-1H-pyrazol-4-yl)-2-picolinamide.

14. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-methyl-1H-pyrazol-4-yl)-2-picolinamide.

15. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-ethyl-1H-pyrazol-4-yl)-2-picolinamide.

16. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-isopropyl-1H-pyrazol-4-yl)-2-picolinamide.

17. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-(1-cyanocyclopropyl)-1H-pyrazol-4-yl)-2-picolinamide.

18. The compound or the pharmaceutically acceptable salt thereof according to claim 1, wherein the compound is N-(1-(1-(1-acetylpiperidin-4-yl)azetidin-3-yl)-3-(difluoromethyl)-1H-pyrazol-4-yl)-6-(1-(1-cyanocyclobutyl)-1H-pyrazol-4-yl)-2-picolinamide.

* * * * *